US006281200B1

(12) United States Patent
Fife et al.

(10) Patent No.: US 6,281,200 B1
(45) Date of Patent: Aug. 28, 2001

(54) FUNCTIONAL CHARACTERIZATION OF THE C-C CHEMOKINE-LIKE MOLECULES ENCODED BY MOLLUSCUM CONTAGIOSUM VIRUS TYPES 1 AND 2

(75) Inventors: Kenneth H. Fife, Zionsville; Michell D. Krathwohl; Robert Hromas, both of Indianapolis; Darron R. Brown, Zionsville; Hal E. Broxmeyer, Indianapolis, all of IN (US)

(73) Assignee: Advanced Research & Technology Institute, Bloomington, IN (US)

( * ) Notice: Subject to any disclaimer, the term of this patent is extended or adjusted under 35 U.S.C. 154(b) by 0 days.

(21) Appl. No.: 09/133,521

(22) Filed: Aug. 13, 1998

Related U.S. Application Data

(60) Provisional application No. 60/055,532, filed on Aug. 15, 1997.

(51) Int. Cl.$^7$ .................................................. C12N 15/39

(52) U.S. Cl. ..................... 514/44; 435/320.1; 435/325; 435/252.3; 536/23.72

(58) Field of Search .................................. 536/23.1, 23.4, 536/23.72; 435/6, 69.1, 69.7, 320.1, 252.3, 325; 514/44

(56) References Cited

PUBLICATIONS

Alkhatib et al., "CC CKR5: a Rantes, MIP–1alpha, MIP–1beta recepotr as a fusion cofactor for macrophage–tropic HIV–1," Science, 272(5270):1955–1958, 1996.
Baba, et al., "Identification of CCR6, the specific receptor for a novel lymphocyte–directed CC chemokine LARC," J. Biol. Chem., 272:14893–14898, 1997.
Baggiolini, et al., "Interleukin–8 and related chemotactic cytokines—CXC and CC chemokines" Adv. Immunol., 55:97–179, 1994.
Bender et al., "Improved methods for the generation of denritic cells from nonproliferating progenitors in human blood," J. Immunol. Meth., 196:121–135, 1996.
Birthistle and Carrington, "Molluscum Contagiosum Virus" J. Infect., 34:21–28, 1997.
Broxmeyer, et al., "Comparative analysis of the human macrophage inflammatory protein family of cytokines (chemokines) on proliferation of human myeloid progenitor cells,"J. Immunol., 150:3448–3458, 1993.
Broxmeyer, et al., "Enhancing and suppressing effects of recombinant murine macrophage inflammatory proteins on colony formation in vitro by bone marrow myelois progenitor cells," Blood, 76:1110–1116, 1990.
Broxmeyer, et al., "Human chemokines: enhancement of specific activity and effects in vitro on normal and leukemic progenitors and a factor–dependent cell line and in vivo in mice," Ann. Hematol., 71:235–246, 1995.
Buller, et al., "Replication of molluscum contagiosum virus", Virology, 213:655–659, 1995.

Caux et al., "GM–CSF and TNF–α cooperate in the generation of dendritic Langerhans cells," Nature, 360:258–261, 1992.
Choe et al., "The beta–chemokine receptors CCR3 and CCR5 facilitate infection by primary HIV–1 isolates," Cell, 85(7):1135–1148, 1996.
Clark–Lewis, et al., "Structure–activity relationships of chemokines", J. Leukocyte Biol., 57:703–711, 1995.
Cocchi, et al., "Identification of RANTES, MIP–1 α, and MIP–1 β as the major HIV–suppressive factors produced by CD8$^+$ T cells", Science, 270:1811–1815, 1995.
Damon, Murphy and Moss, "Broad spectrum chemokine anatagonistic activity of a human poxvirus chemokine homolog," Proc. Natl. Acad. Sci. USA, 95:6403–6407, 1998.
Darai et al., "Analysis of the genome of molluscum contagiosum virus by restriction endonuclease analysis and molecular cloning", J. Med. Virol., 18:29–39, 1986.
Deng et al., "Indentification of a major co–receptor for primary isolates of HIV–1," Nature, 381(6584):661–666, 1996.
Doranz et al., "A dual–tropic primary HIV–1 isolate that uses fusin and the beta–chemokine receptors CKR–5, CKR–3, and CKR–2b as fusion cofactors," Cell, 85(7):1149–1158, 1996.
Dragic et al., "HIV–1 entry into CD4+ cells is mediated by the chemokine receptor CC–CKR–5," Nature, 381(6584):667–673, 1996.
Fenner and Nakano, In: Laboratory Diagnosis of Infectious Diseases, vol. 2, Viral Rickettsial and Chlamydial Disease, Lennette et al., (Eds.) Springer–Verlag, New York (publ.), p177–207, 1988.
Fife et al., "Growth of molluscum contagiosum virus in a human foreskin xenograft model", Virology, 226:95–101, 1996.
Gompels, et al., "The DNA sequence of human herpesvirus–6: structure, coding content, and genome evolution," Virology, 209:29–51, 1995.
Gottlieb and Myskowski, "Molluscum contagiosum," Int. J. Dermatol., 33:453–461, 1994.
Graham et al., "Identification and characterization of an inhibitor of haemopoietic stem cell proliferation," Nature, 344:442–444, 1990.

(List continued on next page.)

Primary Examiner—James Martinell
(74) Attorney, Agent, or Firm—Fulbright & Jaworski

(57) ABSTRACT

The inventors have cloned and expressed the chemokine-like genes from MCV type 1 and the closely related MCV type 2 in order to determine a potential role for these proteins in the viral life cycle. These are the first viral chemokines that have been shown to antagonize the chemotactic activity of human chemokines and the first viral chemokines that have been shown to have inhibitory activity on human hematopoietic progenitor cells. Methods and compositions for exploiting these proteins are disclosed herein.

21 Claims, 4 Drawing Sheets

OTHER PUBLICATIONS

Graham et al., "Uncoupling of stem cell inhibition from monocyte chemoattraction in MIP–1 alpha by mutagenesis of the proteoglycan binding site", *EMBO J.*, 15:6506–6515, 1996.

Grandaliano et al., "Monocyte chemotactic peptide–1 expression and monocyte infiltration in acute renal transplant rejection," *Transplantation*, 63(3):414–420, 1997.

Greaves et al., "CCR6, a CC chemokine receptor that interacts with macrophage inflammatory protein 3 α and is highly expressed in human dendritic cells," *J. Exp. Med.*, 186:837–844, 1997.

Grynkiewicz et al., "A new generation of $Ca^{2+}$ indicators with greatly improved fluorescence properties," *J. Biol. Chem.*, 260:3440–3450, 1985.

Hromas et al., "Cloning and characterization of exodus, a novel β–chemokine," *Blood*, 89:3315–3322, 1997.

Hromas et al., "Isolation and characterization of Exodus–2, a novel C–C chemokine with a unique 37 amino acid carboxyl–terminal extension," *J. Immunol.*, 159:2554–2558, 1997.

Kledal et al., "A broad–spectrum chemokine antagonist encoded by Kaposi's sarcoma–associated herpesvirus," *Science*, 277:1656–1659, 1997.

Krathwohl et al., "Functional characterization of the C–C chemokine–like molecules encoded by molluscum contagiosum virus types 1 and 2," *Proc. Natl. Acad. Sci. USA*, 94:9875–9880, 1997.

MacDonald et al., "Late expression of a β chemokine homolog by murine cytomegalovirus" *J. Virol.*, 71:1671–1678, 1997.

Mantovani et al., "The chemokine superfamily: Crosstalk with the IL–1 system," *Immunobiol.*, 195:522–549, 1996.

Moore et al., "Molecular mimicry of human cytokine and cytokine response pathway genes by KSHV," *Science*, 274, 1739–1744, 1996.

Nicholas et. al., "Kaposi's sarcoma–associated human herpesvirus–8 encodes homologues of macrophage inflammatory protein–1 and interleukin–6," *Nat. Med.*, 3:287–292, 1997.

Oberlin et al., "The CXC chemokine SDF–1 is the ligand for LESTR/fusin and prevents infection by T–cell–line–adapted HIV–1," *Nature*, 382:833–835, 1996.

Pattison et al., "RANTES chemokine expression in cell–mediated transplant rejection of the kidney," *Lancet*, 343(8891):209–211, 1994.

Pattison et al., "RANTES chemokine expression in transplant–associated accelerated atherosclerosis," *J. Heart Lung Transplant*, 15(12)1194–1199, 1996.

Pickup, "Poxviral modifiers of cytokine responses to infection," *Infectious Agents and Disease—Reviews Issues and Commentary*, 3:116–127, 1994.

Porter et al., In: Molecular *and Cell Biology of Sexually Transmitted Diseases.*, Wright and Archard (Eds), Chapman and Hall Ltd. London (publ.), p 233–257, 1992.

Porter et al., "Molluscum contagiosum virus types in genital and non–genital lesions," *Br. J. Dermatol.*, 120:37–41, 1989.

Price et al.,"$α_6$ integrins are required for Langerhans cell migration from the epidermis," *J. Exp. Med.*, 186:1725–1735, 1997.

Ray and Gately III, Dermatologic manifestations of HIV infection and AIDS *Infect. Dis.* Clinics *North Am.*, 8:583–605, 1994.

Senkevich et al., "Genome sequence of a human tumorigenic poxvirus: Prediction of specific host response–evasion genes," *Science*, 273:813–816, 1996.

Senkevich et al., "The genome of molluscum contagiosum virus: Analysis and comparison with other poxviruses," *Viology*, 233(1):19–42, 1997.

Shisler et al., "Ultraviolet–induced cell death blocked by a selenoprotein from a human dermatotropic poxvirus," *Science*, 279:102–105, 1998.

Smith et al., "Cutaneous findings in HIV–1–positive patients: a 42–month prospective study," *J. Am. Acad. Dermatol.*, 31:746–754, 1994.

Takematsu and Tagami, "Proinflammatory properties of molluscum bodies," *Arch. Dermatol. Res.*, 287:102–016, 1994.

Thompson et al., "Molecular epidemiology of Australian isolates of molluscum contagiosum," *J. Med. Virol.*, 32:1–9, 1990.

Weiss et al., "An essential role for CD44 variant isoforms in epidermal Langerhans cell and blood dendritic cell function," *J. Cell. Biol.*, 137:1137–1147, 1997.

Wolpe et al., "Macrophages secrete a novel heparin–binding protein with inflammatory and neutrophil chemokinetic properties," *J. Exper. Med.*, 167:570–581, 1988.

Bugert et al., "Chemokine homolog of Molluscum contagiosum virus: Sequence conservation and expression," *Virology*, 242(1):51–59, 1998.

International Search Report dated Dec. 22, 1998 (PCT/US98/16845)(INDY:034P).

Wallace et al, Methods Enzymol. 152: 432 (1987).*

Critical Synergy: The Biotechnology Industry and Intellectual Property Protection, Biotechnology Industry Organization, 1994, Washington, DC, pp. 75 and 100–107.*

* cited by examiner

```
MCV TYPE 1    1 ATGAGGGGCGGAGACGTCTTCTTCGGCGAGCGTTGTCTTGATGCTGTTACTTGCACTACCGGCGACCGGGAGTGTCACTCGGCGAGACGGAAATGTTGTTTGAA
MCV TYPE 2    1 ATGAGGGGCCAGAGCGTCTTCGGCGAGCCGTTGTCTTGACGCTGTTACTTGCACTACCGCGACCGGGAGTGTCACTCTCGAGACGGAAATGTTGTTTGAA

99 TCCCACAAATCGTCCGATCCCGAATCCTTTACTGCAAGATCTATCACGCGTCGACTATCAGGCGATAGGACATGACTGCGGACGGGAAGCTTTCAGAGTGACGCTGCAA
             99 TCCTACAAATCGTCCGATACCGAGGCCTTTACTGCAAGATCTAGACAAAGTCGATTATCAGCCGATGGGACATGACTGCGGACGGGAAGCTTTCAGAGTGACGCTGCAA

208 GACGGAAGACAAGGCTGCGTTAGCGTTGGTAACAAGAGCTTACTAGACTGGCTTCGGGGACACAAGGATCTCTGCCCTCAGATATGGTCCGGTGCGAGTCTCTGTAA
            208 GACGGAAGACAAGGCTGTGTTAGCGTTGGTAACCAGAGTTTACTAGACTGGCTGAAGGGACACAAGGATCTCTGCCCGGGATGTGGCCGGGTGCGGAGTCTCTGTAA
```

*FIG. 1A*

Active Site

```
MC148R1 PROTEIN  1 MRGGDVFASVVLMLLL.ALPRPGVS.......LARRKCCLNPTNRPIPNPLLQDLSRVDYQAIGHDCGREAFRVTLQDGRQGCVSVGN
MC148R2 PROTEIN  1 MRARAVFASVVLTLLL.ALPRPGVS.......LSRRKCCLNPTNRPIPRPLLQDLDKVDYQPMGHDCGREAFRVTLQDGRQGCVSVGN
MCP 1 PROTEIN    1 M...KVSAALLCLLLT.VAAFSTEVLAQPDAINSQVACCYTFNSKKISMQRLMNYRRV....TSSKCPKEAVIFKTILGKELCADPKQ
MIP 1β PROTEIN   1 M....KLCVTVLSLLMLVAAFCSPALSAPMGSDPPTACCFSYTAR.....KLPRNFVVDYYETSSLCSQPAVVFQTKRSKQVCADPSE
MIP 1α PROTEIN   1 M....QVSTAALAVLLCTMALC.NQFSASLAADTPTACCFSYTSR.....QIPQNFIADYFETSSQCSKPGVIFLTKRSRQVCADPSE
```

Proteoglycan Binding Site

```
MC148R1 PROTEIN 88 KSLLDWLRGHKDLCPQIWSGCESL
MC148R2 PROTEIN 88 QSLLDWLKGHKDLCPRMWPGCESL
MCP 1 PROTEIN   88 KWVQDSINYLNKKNQTPKP
MIP 1β PROTEIN  88 SWVQEYVYDLELN
MIP 1α PROTEIN  88 EWVQKYVSDLELSA
```
                                             ↑                                              ┌──────────────

FUNCTIONAL CHARACTERIZATION OF THE C-C CHEMOKINE-LIKE MOLECULES ENCODED BY MOLLUSCUM CONTAGIOSUM VIRUS TYPES 1 AND 2

The present application is a continuation-in-part of co-pending U.S. Provisional Patent Application Serial No. 60/055,532 filed Aug. 15, 1997. The entire text of the above-referenced disclosure is specifically incorporated by reference herein without disclaimer.

The government may own rights in the present invention pursuant to grant numbers HL56416; HL54037; HL53586 from the National Institutes of Health

BACKGROUND OF THE INVENTION

1. Field of the Invention

The present invention relates generally to the fields of inflammatory responses and natural chemokine action. More particularly, it concerns the methods of making and using of novel chemokine-like genes and proteins from MCV type 1 and the closely related MCV type 2.

2. Description of Related Art

Poxviruses are notorious for their ability to evade the host's immune system by both active and passive mechanisms (Pickup, 1994). Since the eradication of smallpox, the only poxvirus that naturally infects humans is molluscum contagiosum virus (MCV). MCV causes benign proliferative lesions of the skin in normal and immunocompromised individuals. Persons with acquired immune deficiency syndrome (AIDS) sometimes get extensive MCV infections which can be disfiguring (Ray and Gateley III, 1994; Smith et al., 1994).

There are at least two types of MCV based on restriction endonuclease cleavage patterns of viral DNA (Darai et al., 1986; Porter et al., 1989; Thompson et al., 1990). Some epidemiological studies have been reported, but there is no consensus on anatomic or patient group distribution of the two MCV types. Although MCV cannot be propagated in tissue culture, the inventors and others have shown recently that MCV can be grown in human tissue implanted into immunodeficient mice (Buller et al., 1995; Fife et al., 1996).

Recently, much attention has been focused on chemokines, small proteins produced by lymphocytes and a variety of other cells. Chemokines were originally identified by their ability to attract inflammatory cells, but they have since been shown to have a variety of additional activities (for review, see Baggiolini et al., 1994). In addition to chemotaxis, some chemokines have been shown to cause decreased growth of hematopoietic stem and early subsets of myeloid progenitor cells (Broxmeyer et al., 1995; Broxmeyer et al., 1993; Broxmeyer et al., 1990; Graham et al., 1990) and some have been shown to block entry of human immunodeficiency virus into lymphocytes (Cocchie et al., 1995; Oberlin et al., 1996). Roles for chemokines in a variety of allergic and autoimmune diseases have also been postulated, although direct evidence is limited (for review see Mantovani et al., 1996).

It has been assumed that MCV, like other poxviruses, has immune evasion functions. The recent report of the nucleotide sequence of the MCV genome (Senkevich et al., 1996) has permitted identification of potential candidate viral proteins that may be involved in escape from the host immune system. One such putative viral protein is designated MC148R. This open reading frame potentially encodes a 104 amino acid protein with significant homology to β chemokines such as macrophage inflammatory protein (MIP)-1β (SEQ ID NO:6). The putative MC148R protein contains a five amino acid deletion at the functionally important amino terminus of the mature protein, relative to MIP-1β (Senkevich et al., 1996). Only three other viruses, human herpes virus 6 (Gompels et al., 1995), human herpes virus 8 (Moore et al., 1996; Nicholas, 1997) and murine cytomegalovirus (MacDonald et al., 1997) are known to encode chemokine analogs. These herpesvirus chemokine analogs do not contain deletions, although there is only limited information about their ability to function as chemokine agonists.

There are important issues regarding this MCV viral protein that need to be resolved. It needs to be determined whether this protein may act as a chemokine agonist, if so, are there other chemokines agonists expressed by MCV. The pathogenic role of MCV viral proteins play is unknown. Further there is little information on how MCV infection escapes immune attack from the host, the presence of MCV viral protein and other proteins related to this protein may somehow effect immune system escape. The answers to these question would have many benefits in the treatment of viral infection as well as effecting immune escape in cells in which it would be desirable to suppress the host immune system.

SUMMARY OF THE INVENTION

The present invention provides an isolated and purified chemokine-like protein. In a particular embodiment the preferred polypeptide has the sequence of SEQ ID NO:2. In yet another embodiments the preferred polynucleotide has the sequence of SEQ ID NO: 1. In certain embodiments, the present invention provides a peptide of about 10 to about 50 contiguous amino acids of SEQ ID NO:2. In preferred embodiments, the peptide is about 10 amino acids in length. In other preferred embodiments, the peptide may be independently, about 15 amino acids in length, about 20 amino acids in length, about 25 amino acids in length, about 50 amino acids in length or about 100 amino acids in length.

The present invention also provides an isolated and purified nucleic acid encoding the chemokine-like protein having an amino acid sequence as set forth in SEQ ID NO:2. In particularly preferred embodiments, the nucleic acid sequence is as set forth in SEQ ID NO: 1 or the complement thereof. In certain embodiments, the present invention provides an oligonucleotide of about 15 to about 50 contiguous base pairs of SEQ ID NO: 1, or the complement thereof. In other preferred the oligonucleotide may be independently about 15 base pairs in length, about 20 base pairs in length, about 25 base pairs in length, about 50 base pairs in length, about 100 base pairs in length or about 200 base pairs in length A purified antibody that is immunoreactive with a chemokine-like MCV viral protein is also provided by the present invention. In particular embodiments, the MCV viral protein has an amino acid sequence as set forth in SEQ ID NO:2, in other embodiments, the MCV viral protein has an amino acid sequence as set forth in SEQ ID NO:4.

In another aspect of the present invention there is provided an expression construct comprising a vector comprising an isolated polynucleotide encoding a chemokine-like MCV viral protein and a promoter operably linked to the isolated polynucleotide.

In preferred embodiments, the vector may be a viral vector. In preferred embodiments, the viral vector may be selected from the group consisting of a retroviral vector, an adenoviral vector, a herpesviral vector, adeno-associated viral vector and a cytomegaloviral vector. In other embodiments, the viral vector further comprises a polyadenylation signal. In other preferred embodiments, the expression construct encodes an MCV viral protein that has an amino acid sequence as set forth in SEQ ID NO:2. In other embodiments, the MCV viral protein has an amino acid sequence as set forth in SEQ ID NO:4.

In specific embodiments, the promoter is selected from the group consisting of CMV IE, SV40 MLP, AdE1, keratin 10 promoter, baculovirus polyhedrin promoter and β-actin.

Also provided is a recombinant host cell comprising with a vector comprising an expression region encoding a chemokine-like MCV viral protein operatively linked to a promoter.

The present invention also describes a method for treating MCV induced proliferative lesions of the skin in an individual comprising inhibiting the activity of chemokine-like MCV viral protein in the lesion. In particular aspects, the inhibiting comprises contacting the lesion with an inhibitor of chemokine-like MCV viral proteins. In certain embodiments, the inhibitor comprises a vector comprising an expression cassette comprising a gene encoding MCV viral protein placed antisense to and operatively linked to a promoter; wherein expression construct inhibits the function of chemokine-like MCV viral protein. In other embodiments, the method may further comprise administering to the individual an inhibitor of chemokine-like MCV viral protein activity identified according to a method comprising the steps of (i) providing a cell expressing an MCV viral protein; (ii) contacting the cell with a candidate substance; (iii) measuring the activity of the MCV viral protein in the cell; and (iv) comparing the activity of the protein in the cell of step (iii) with the activity of the protein in the cell of step (i); wherein a decrease in the activity of the protein in the cell of step (iii) indicates that the substance is an inhibitor of MCV viral protein activity. In more particular embodiments, the individual may be immunocompromised. In yet more particular embodiments, the individual has HIV infection.

There also is provided herein a method of inhibiting the action of human chemokines in a cell comprising contacting the cell with a composition comprising a chemokine-like MCV viral protein. In particular aspects, the inhibiting comprises contacting the cell with a vector comprising an expression cassette comprising a gene encoding a chemokine like MCV viral protein operatively linked to a promoter; wherein expression of the protein inhibits the chemokine response in the cell.

In a further aspect of the present invention, there is provided a method for treating a chemokine-mediated disease in a subject comprising the steps of providing a vector comprising an expression cassette comprising a gene encoding a chemokine-like MCV viral protein and a promoter active in eukaryotic cells, wherein the gene is operably linked to the promoter; contacting the vector with the subject under conditions permitting uptake of the vector by the subject; wherein expression of the protein in the subject effects a treatment of the disease.

The present invention further provides a pharmaceutical composition comprising a vector construct comprising an expression region encoding an MCV viral protein under the control of a eukaryotic promoter; and a pharmaceutically acceptable carrier, excipient or diluent.

A method of protecting bone marrow cells from chemotherapy is also provided herein wherein said method comprises administering a composition comprising a chemokine-like MCV viral protein in an effective to prevent the proliferation of the cells. In particular aspects, the composition comprises a vector construct comprising an expression region encoding a chemokine-like MCV viral protein under the control of a eukaryotic promoter.

In yet another aspect of the present invention there is provided a method of screening for a modulator of inflammatory response comprising the steps of (i) providing a cell expressing an MCV viral protein; (ii) contacting the cell with a candidate substance; (iii) measuring the activity of the MCV viral protein in the cell; and (iv) comparing the activity of the protein in the cell of step (iii) with the activity of the protein in the cell of step (i), wherein an alteration in the activity of the protein in the cell of step (iii) indicates that the candidate substance is a modulator of inflammatory response.

In still another aspect, the present invention provides a modulator of inflammatory response identified according to a method comprising the steps of (i) providing a cell expressing an MCV viral protein; (ii) contacting the cell with a candidate substance; (iii) measuring the activity of the MCV viral protein in the cell; and (iv) comparing the activity of the protein in the cell of step (iii) with the activity of the protein in the cell of step (i), wherein an alteration in the level of the protein in the cell of step (iii) indicates that the candidate substance is a modulator of inflammatory response.

Another aspect of the present invention provides a method of blocking an inflammatory response in an individual comprising administering to the individual a composition comprising a chemokine-like MCV-viral protein. In particular aspects it is contemplated that the composition comprises a vector construct comprising an expression region encoding a chemokine-like MCV viral protein under the control of a eukaryotic promoter, wherein expression of the MCV viral protein blocks the inflammatory response in the subject. In particularly preferred embodiments, the method may further comprise administering to the individual an enhancer of chemokine-like MCV viral protein activity identified according to a method comprising the steps of (i) providing a cell expressing a chemokine-like MCV viral protein; (ii) contacting the cell with a candidate substance; (iii) measuring the activity of the chemokine like MCV viral protein in the cell; and (iv) comparing the activity of the protein in the cell of step (iii) with the activity of the protein in the cell of step (i), wherein an increase in the activity of the protein in the cell of step (iii) indicates that the substance is an enhancer of chemokine-like MCV viral protein activity.

In another aspect, the present invention provides a method of inhibiting transplant rejection in an individual comprising administering to the individual a composition comprising a chemokine-like MCV viral protein, wherein the presence of the protein prevents the chemokine-mediated attack of the transplant. In particularly preferred embodiments, the composition comprises a vector construct comprising an expression region encoding a chemokine-like MCV viral protein under the control of a eukaryotic promoter, wherein expression of the MCV viral protein blocks the inflammatory response in the subject. In more specific embodiments, the chemokine mediated attack is mediated by a chemokine selected from the group consisting of RANTES, MIP-1α and MCP-1.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A and FIG. 1B. (FIG. 1A) Complete nucleotide sequences of MC148R1 and MC148R2 regions, showing sequence alignments. Note that the sequence of MC148R1 is identical to that previously reported (Senkevich et al., 1996). The MC148R2 sequence has been deposited in GenBank (accession number U96749). (FIG. 1B) Predicted protein sequences of MC148R1 (SEQ ID NO:4) and MC148R2 (SEQ ID NO:2), showing sequence alignments with MIP-1β (SEQ ID NO:6), MCP-1 (SEQ ID NO:5) and MIP-1α (SEQ ID NO:7). Putative active sites are highlighted and the predicted signal peptide cleavage sites are indicated by vertical arrows.

(FIG. 2A) Results for MC148R1 shown as protein alone and in competition with MIP-1α. (FIG. 2B) Results for MC148R2. (FIG. 2C) Results for pVL vector control protein preparation. Note that in each panel the viral protein (or vector control) alone bars are at or near the baseline.

(FIG. 3A) Effects on CFU-GM colony formation. Control colonies consist of media alone. MC148R1 and MC148R2 were added to media and serially diluted. (*)=p<0.01 when compared to control. (FIG. 3B) Effects on BFU-E colony formation, (*)=p<0.01. (FIG. 3C) Effects on CFU-GEMM colony formation. (*)=p<0.0 1. The results shown are the average of three separate studies in which the control number of CFU-GM, BFU-E, and CFU-GEMM colonies of individual studies (respectively) ranged from 44±7 to 69±3, 24±5 to 84±7, and 16±3 to 18±3.

DESCRIPTION OF ILLUSTRATIVE EMBODIMENTS

I. The Present Invention

Figure 2A:
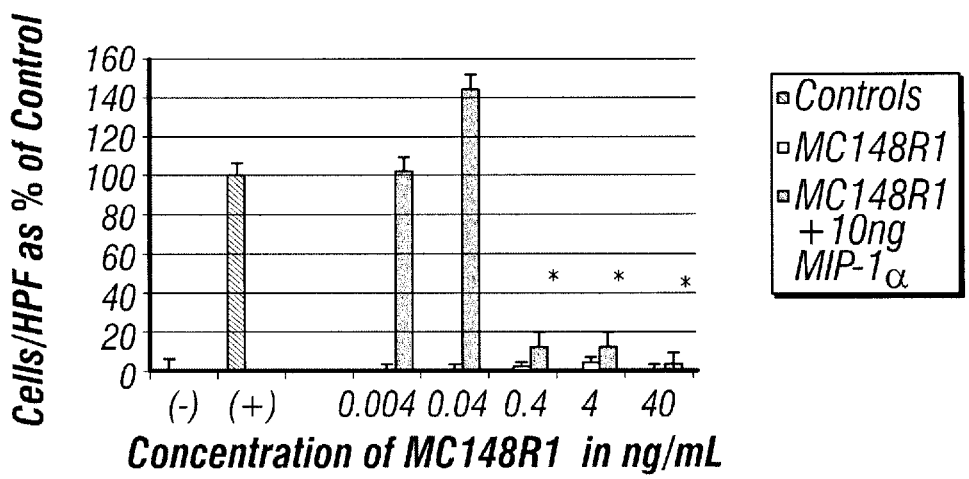
FIG. 2A, FIG. 2B and FIG. 2C. Results of chemotaxis assays. Negative controls consisted of media alone, while positive controls consisted of media and 10 ng of MIP-1α. Concentrations of the viral proteins are for the partially purified protein preparations, and include protein impurities in the total concentration. (*)=p<0.05 when compared to positive controls; HPF=high power field. Results are expressed as percentages of the positive control above baseline and represent the mean of at least two independent studies. The number of cells migrating in the positive control varied among different studies but ranged from 50 to 80 cells.

Many viruses have evolved mechanisms for evading the host immune system by synthesizing proteins that interfere with the normal immune response. The poxviruses are among the most accomplished at deceiving their hosts' immune systems. The nucleotide sequence of the genome of the human cutaneous poxvirus, molluscum contagiosum virus (MCV) type 1, was recently reported to contain a region that resembles a human chemokine.

Like many other poxviruses, molluscum contagiosum probably uses a variety of methods to escape the immune system. The inventors have demonstrated evidence of a novel mechanism for escape from immune system surveillance, namely, blocking the signal for migration of effector cells to the site of infection. The inventors have also shown that MCV 2 contains a chemokine-like gene that is very similar to the MCV 1 counterpart at the DNA and protein level. Both viral chemokine-like proteins tested are quite potent in their ability to block chemotaxis by MIP-1α, a property necessary for a successful competitive inhibitor. The inventors' studies may underestimate the potency of the inhibitory effects because the inventors' viral chemokine preparations were only partially purified. Neither viral protein exhibits chemotactic properties even at high concentrations. Lesions in vivo are characterized by a lack of inflammatory cell infiltrates, consistent with a mechanism for immune system escape (Birthistle, 1997). Neither T-cells nor natural killer cells are found at the base of molluscum lesions (Viac, 1990). Furthermore, lesions undergoing spontaneous resolution often show mononuclear cell infiltrates, confirming that these types of cells are critical in the immune response to molluscum contagiosum (Gottlieb and Myskowski, 1994). Other studies have shown that mature molluscum lesions contain the C-X-C chemokines GROα and IL-8 within the molluscum body itself that are released on decomposition (Takematsu, 1994). It is possible that the immune response is blocked by chemokine antagonists early in infection, but later the physical barrier of the molluscum body prevents detection by the immune system. Further studies on the patterns of expression of these viral chemokines are needed to clarify this issue.

The deletion present at the amino terminus of MC148R with respect to MIP-1β and MCP-1 may explain the biologic behavior observed in these studies. Previous reports on structure-function relationships of the C—C chemokines showed that for MCP-1, the first five amino acids constitute the "activation site" and the next five constitute the "binding site" (Clark-Lewis, 1995). The deletion of the first 5 amino acids in the viral proteins would then result in a protein that has only the binding site, and would thus not be expected to activate the receptor. Alternatively, a proposed internal site named the proteoglycan binding site may explain the lack of chemotaxis. One mutational analysis of MIP-1α showed that placing neutral or acidic amino acids at this site resulted in the loss of chemotaxis, while maintaining other chemokine functions (Graham et al., 1996). Curiously, both viral proteins contain neutral or acidic amino acids at this site. This change probably accounts for the observation that the viral chemokines elute from heparin sepharose at a lower salt concentration (0.25 M) than that required to elute other chemokines such as MIP-1α (0.6 M; Wolpe et al., 1988). The relative importance of this internal site versus the amino terminal deletion of the viral proteins is not clear.

The inhibitory effect of chemokines on hematopoietic stem and progenitor cells has been studied intensely. A number of studies suggest a regulatory role for chemokines in hematopoiesis (reviewed in Broxmeyer et al., 1995). It is not known if these viral proteins reach the bone marrow during natural infection, so the effect on hematopoietic cells may not be relevant to molluscum contagiosum virus pathogenesis. However, the fact that the viral proteins do inhibit hematopoiesis suggests that they are able to activate at least some chemokine receptors, and could have clinically relevant effects on other cell types. At present, it is not clear which portion of the chemokine protein is responsible for inhibiting hematopoiesis. Consistent with previous studies is the fact that modification of the proteoglycan binding site does not have an effect on inhibition of hematopoiesis (Graham et al., 1996). The inhibition of hematopoiesis would then be due to another active site that is retained in the viral proteins.

This study is the first report of a viral chemokine that blocks the chemotactic activity of natural chemokines. This novel mechanism of immune escape has not previously been described for any other virus, and underscores the importance of chemokines in natural infection. These are also the first viral chemokines that have been shown to block growth of hematopoietic progenitor cells. Thus, compositions of the present invention will be useful in blocking the proliferation of hematopoietic progenitor cells where the growth of such cells is detrimental to the subject. For example, the compositions of the present invention may be used to inhibit chemotoxicity in bone marrow cells, when chemotherapeutic agents are being applied to treat various cancers.

The inventors have cloned and expressed these chemokine-like genes from MCV type 1 and the closely related MCV type 2 in order to determine a potential role for these proteins in the viral life cycle. In monocyte chemotaxis assays, the viral proteins have no chemotactic activity but both viral proteins block the chemotactic response to the human chemokine, macrophage inflammatory protein (MIP)-1α (SEQ ID NO:7). Like MIP-1α, both viral proteins also inhibit the growth of human hematopoietic progenitor cells but the viral proteins are more potent in this activity than the human chemokine.

These are the first viral chemokines that have been shown to antagonize the chemotactic activity of human chemokines and the first viral chemokines that have been shown to have inhibitory activity on human hematopoietic progenitor cells. The inventors suggest that the inhibition of chemotaxis is an immune evasion function of these proteins during molluscum contagiosum virus infection.

Thus, the present invention provides a nucleotide sequence uniquely identifying a novel chemokine-like protein that acts as an antagonist of the C—C family, of chemokines. This protein is expressed in MCV cells and has been shown herein to inhibit the action of human chemokines. Thus, the nucleic acids, polypeptides and antibodies to the polypeptides of the present invention will be useful in diagnostic assays based on the inhibition of human chemokine production in cases of inflammation or disease that are mediated by human chemokine action.

Excessive expression of chemokines leads to activation of monocytes, macrophages, basophils, eosinophils, T lymphocytes and/or other cells in humans which respond by producing abundant proteases and other molecules which can lead to tissue damage or destruction. Therefore, a composition that can inhibit the action of these chemokines can effect treatment of an abnormal condition caused by the overexpression of chemokines in, for example, asthma, Hodgkins disease, inflamed adenoids, tonsilitis, Epstein-Barr virus, pneumonia, myocarditis, rheumatoid arthristis and other autoimmune diseases.

Furthermore, the MCV chemokine-like compositions of the present invention will be useful in identifying compounds to treat against viral or bacterial infections including mononucleosis, malaria or AIDS; mechanical injury associated with trauma; diseases affecting immunoregulation such as rheumatoid arthritis or systemic lupus erythematosis; diseases of erythrocytes or blood flow including sickle cell anemia and beta thalassemia; infiltrative diseases such as leukemias and lymphomas; or other physiologic and pathologic problems which affect the function of the organ.

II. The Action of Chemokines

Leukocytes including monocytes, macrophages, basophils, and eosinophils play important roles in the pathological mechanisms initiated by T and/or B lymphocytes. Macrophages, in particular, produce powerful oxidants and proteases which contribute to tissue destruction and secrete a range of cytokines which recruit and activate other inflammatory cells.

The current model of leukocyte movement or trafficking from the blood to injured or inflamed tissues comprises the following steps. The first step is the rolling adhesion of the leukocyte along the endothelial cells of the blood vessel wall. This movement is mediated by transient interactions between selectins and their ligands. A second step involves cell activation which promotes a more stable leukocyte-endothelial cell interaction mediated by the integrins and their ligands. This stronger, more stable adhesion precipitates the final steps-leukocyte diapedesis and extravasation into the tissues.

The chemokine family of polypeptide cytokines, also known as intercrines, possesses the cellular specificity required to explain leukocyte trafficking in different inflammatory situations. First, chemokines mediate the expression of particular adhesion molecules on endothelial cells; and second, they generate gradients of chemoattractant factors which activate specific cell types. In addition, the chemokines stimulate the proliferation of specific cell types and regulate the activation of cells which bear specific receptors. Both of these activities demonstrate a high degree of target cell specificity The chemokines are small polypeptides, generally about 70–100 amino acids in length, 8–11 kD in molecular weight and active over a 1–100 ng/ml concentration range. Initially, they were isolated and purified from inflamed tissues and characterized relative to their bioactivity. More recently, chemokines have been discovered through molecular cloning techniques and characterized by structural as well as functional analysis.

The chemokines are related through a four cysteine motif which is based primarily on the spacing of the first two cysteine residues in the mature molecule. Currently the chemokines are assigned to one of two families, the C-X-C chemokines (alpha) and the C—C chemokines (beta). Although exceptions exist, the C-X-C chemokines generally activate neutrophils and fibroblasts while the C—C chemokines act on a more diverse group of target cells which include monocytes/macrophages, basophils, eosinophils, T lymphocytes and others. The known chemokines of both families are synthesized by many diverse cell types as reviewed in Thomson A. (1994) The Cytokine Handbook, 2d Ed. Academic Press, New York. The two groups of chemokines will be described in turn.

The most extensively studied C-X-C chemokine is platelet factor 4 (PF4) is a typical C-X-C chemokine. It is a 70 amino acid protein that displays the definitive four cysteines and is released along with platelet derived growth factor (PDGF), transforming growth factor beta (TGF-β) and beta -thromboglobulin (β-TG) from the granules of stimulated platelets. This homotetrameric molecule shares structural similarity with interleukin-8 (IL-8), induces the migration of fibroblasts, neutrophils and monocytes, and binds heparin. PF4 provides the biological model for a link among thrombosis, inflammation, and wound healing. Other chemokines found in the platelet α granule include beta-TG, connective tissue activating protein III (CTAP-III) and neutrophil activating peptide 2 (NAP-2). All three peptides are derived from the differential processing of a precursor molecule, platelet basic protein (PBP). beta-TG is an 81 amino acid, highly basic protein which influences the migration of fibroblasts but has no effect on neutrophils or monocytes. CTAP-III is 85 amino acid long, and amino acid 4–85 are identical to beta-TG. Since CTAP-III is the primary protein in the a granule and its role as a purified protein has not elucidated, it may be a secondary precursor, inactive until further processed. NAP-2 appears to attract neutrophils but not monocytes.

Nonplatelet C-X-C chemokines include IL-8, gamma interferon inducible protein (IP-10), melanocyte growth stimulatory activity (MGSA or gro) proteins, epithelial derived neutrophil attractant-78 (ENA-78), granulocyte chemotactic protein-2 (GPC-2) and stromal cell-derived factors-1 alpha and 1 beta (SDF-1 alpha and -1 beta). IL-8 (also know as NAP-1) is secreted by monocytes/macrophages, neutrophils, fibroblasts, endothelial cells, keratinocytes and T lymphocytes in response to proinflammatory cytokines, IL-1 and 3, IFN-gamma and TNF, as well as endotoxin, mitogens, parciculates, bacteria and viruses. IL-8 stimulates acute inflammation including the upregulation of both neutrophil adhesion and keratinocyte growth and the downregulation of histamine production by basophils.

IP-10 is a 10 kD protein of undefined function whose mRNA has been found in monocytes, fibroblasts and endothelial cells. Monocytes, keratinocytes and activated T-cells secrete IP-10 protein which has been localized to sites of delayed hypersensitivity reactions. The cDNA of MGSA/gro alpha produces a 15 kD protein which appears in fibroblasts. Its transcription is growth related, and it functions as an autocrine growth factor. The distinct and non-allelic forms, gro beta and gro gamma are 90% and 86% identical to gro alpha, respectively. Recombinant gro alpha proteins attract and activate neutrophils. ENA-78 was purified from supernatants of lung alveolar cells. Like gro alpha, it attracts and activates neutrophils in vitro.

GCP-2 is a 6 kD protein isolated from the supernatants of osteosarcoma cells. GCP-2 exists in various N-terminally truncated forms, and it attracts and activates neutrophils in vitro and causes granulocyte accumulation in vivo. SDF-1 alpha and —1 beta are newly isolated cDNAs which encode secreted molecules and type I membrane proteins.

At this time, the C—C chemokines number fewer than the C-X-C chemokines, and they appear to have less N-terminal processing. A brief description of the known human (and/or murine) C—C chemokines follows. The macrophage inflammatory proteins alpha and beta (MIP-1-$\alpha$ and $\beta$) were first purified from stimulated mouse macrophage cell line and elicited an inflammatory response when injected into normal tissues. At least three distinct and non-allelic genes encode human MIP-1-$\alpha$ and seven such genes encode MIP-1-$\beta$.

MIP-1 alpha and MIP-1 beta consist of 68–69 amino acid which are about 70% identical in their acidic, mature secreted forms. They are both expressed in stimulated T cells, B cells and monocytes in response to mitogens, anti-CD3 and endotoxin, and both polypeptides bind heparin. While both molecules stimulate monocytes, MIP-1 alpha chemoattracts the CD-8 subset of T lymphocytes and eosinphils, while MIP-1 beta chemoattracts the CD-4 subset of T lymphocytes. In mouse, these proteins are known to stimulate myelopoiesis.

I-309 was cloned from a human gamma—delta T cell line and shows 42% amino acid identity to T cell activation gene 3 (TCA3) cloned from mouse. There is considerable nucleotide homology between the 5' flanking regions of these two proteins, and they share an extra pair of cysteine residues not found in other chemokines. Such similarities suggest I-309 and TCA3 are species homologs which have diverged in sequence and function.

RANTES is another C—C chemokine which is expressed in T cells (but not B cells), in platelets, in some tumor cell lines, and in stimulated rheumatoid synovial fibroblasts. In the latter, it is regulated by interleukins-1 and -4, transforming nerve factor and interferon-gamma. The cDNA cloned from T cells encodes a basic 8 kD protein which lacks N-linked glycosylation and is able to affect lymphocytes, monocytes, basophils and eosinophils. The expression of RANTES mRNA is substantially reduced following T cell stimulation.

Monocyte chemotactic protein (MCP-1) is a 76 amino acid protein which appears to be expressed in almost all cells and tissues upon stimulation by a variety of agents. The targets of MCP-1, however, are limited to monocytes and basophils in which it induces a MCP-1 receptor: G protein-linked calcium flux. Two other related proteins (MCP-2 and MCP-3) were purified from a human osteosarcoma cell line. MCP-2 and MCP-3 have 62% and 73% amino acid identity, respectively, with MCP-1 and share its chemoattractant specificity for monocytes.

In particular, the inflammatory chemokines are capable of inducing localized inflammation when administered subcutaneously such inflammation is characterized by polymorphonuclear cell infiltration, the compositions of the present invention may be employed to reduce this inflammation, reduce the polymorphonuclear infiltration or otherwise inhibit or abrogate the function of human cytokines. Also, cytokines cause in vitro polymorphonuclear cell chemokinesis, which are reflective of the influence of a cytokine involved in mobilization by the mammalian host against an invasive stimulus, and are therefore responsible in, for example, in organ transplant rejection. Indeed, mononuclear cell infiltration is a common histopathological feature of acute renal transplant rejection, in which it seems to play a key role in the pathogenesis of tubulointerstitial lesions (Grandaliano et al., 1997). In the Grandaliano et al., study it was concluded that MCP-1 likely plays a critical role in modulating monocyte influx and consequent tubulointerstitial damage in acute rejection. In yet another study, Pattison et al., (1994; 1996) showed that RANTES was expressed during cell-mediated transplant rejection with the RANTES mRNA being detected in infiltrating mononuclear cells and renal tubular epithelium, and RANTES protein being localized to mononuclear cells, tubular epithelium, and vascular endothelium. This study suggested that RANTES has a role in allograft rejection.

Chemokines have also been implicated in the blocking of HIV entry into the lymphocyte. It appears that the C—C chemokine receptor (CCR)-5 is the principal co-receptor of the macrophage (M$\phi$)-tropic human immunodeficiency virus (HIV)-1 (Cocchi et al., 1995; Deng et al., 1996; Dragic et al., 1996; Alkhatib et al., 1996; Choe et al., 1996; Doranz et al., 1996). In light of the foregoing data it would be therapeutically beneficial to prevent HIV-1 binding to the C—C receptors and thereby prevent HIV-1 infection of cells. Thus, the compositions of the present invention may be used to bind to the C—C receptors and prevent the binding and entry of the HIV infective entity.

Current techniques for diagnosis of abnormalities in the inflamed or diseased tissues mainly rely on observation of clinical symptoms or serological analyses of body tissues or fluids for hormones, polypeptides or various metabolites. Patients often manifest no clinical symptoms at early stages of disease or tumor development. Furthermore, serological analyses do not always differentiate between invasive diseases and genetic syndromes which have overlapping or very similar ranges. Thus, development of new diagnostic techniques comprising small molecules such as the expressed chemokines are important to provide for early and accurate diagnoses, to give a better understanding of molecular pathogenesis, and to use in the development of effective therapies.

In its primary aspect, the present invention concerns the isolation and identification of a particular factor hereinafter referred to as chemokine-like MCV viral proteins, that has been found in MCV infections and are believed to be an inhibitors of human chemokines such as macrophage inflammatory protein, MIP-1. The presence of such chemokine-like MCV viral proteins characteristically aid the MCV infection in escaping from the host immune response system. The present invention also pertains to the use of the MCV viral protein compositions in order to treat a variety of chemokine mediated inflammatory diseases.

III. Chemokine-like MCV Polypeptides and Fragments Thereof

Thus, according to one aspect of the present invention, the present inventors provide the primary sequence for the MC148R1 (also referred to herein as MCV type 1 protein) and MC148R2 (also referred to herein as type 2 protein) chemokine-like MCV viral proteins. These molecules will prove useful in a variety of different contexts. For example, MC148R1 and MC148R2 may be used as an antigens to raise antibodies that can, in turn, be used to study and diagnosis disease states relating to MCV infection. MC148R1 and MC148R2 also can be used as part of screening assays to examine reagents for their ability to affect MCV infection in vitro or in vivo. Furthermore, the inventors have shown that these proteins are capable of mediating immune system escape by inhibiting the action of human chemokines, thus in preferred embodiments, the MC148R1 and MC148R2 compositions of the present invention may be used to inhibit the action of human chemokines.

In addition to the entire MC148R2 molecule, the present invention also relates to fragments of the polypeptide that may or may not retain the chemokine antagonist (or other) activity. Fragments including the N-terminus of the molecule may be generated by genetic engineering of translation stop sites within the coding region (discussed below). Alternatively, treatment of the MC148R1 and MC148R2 molecule with proteolytic enzymes, known as protease, can produces a variety of N-terminal, C-terminal and internal fragments. Examples of fragments may include contiguous residues of the MC148R1 and MC148R2 sequences given in SEQ ID NO:2 and SEQ ID NO:4, of 6, 7, 8, 9, 10, 11, 12, 13, 14, 15, 16, 17, 18, 19, 20, 21, 22, 23, 24, 25, 30, 35, 40, 45, 50, 55, 60, 65, 75, 80, 85, 90, 95, 100, or more amino acids in length. These fragments may be purified according to known methods, such as precipitation (e.g., ammonium sulfate), HPLC, ion exchange chromatography, affinity chromatography (including immunoaffinity chromatography) or various size separations (sedimentation, gel electrophoresis, gel filtration).

A. Structural Features of the Polypeptide

The gene for MCV type 2 protein encodes a 104 amino acid protein (SEQ ID NO:2) with a predicted molecular mass of about 10 kDa. The inventors have demonstrated that the protein has 89% homology to the type 1 sequence. Amino acid comparisons showed 87% homology of the complete sequences, and 86% when the putative leader sequence was removed. The four conserved cysteine residues characteristic of C—C chemokines appear to be conserved in both of the MCV 1 and MCV 2 proteins. Based on sequence comparisons with MCP-1, the first 24 amino acids compose a leader sequence and the next five amino acids constitute the active site. This contrasts to MCP-1 (SEQ ID NO:5) which has 10 amino acids at the amino-terminal active site. MCV type 1 and MCV type 2 have very similar amino acid composition at the putative active site, except for a serine in MCV 2 instead of an alanine at position 26. Both proposed signal peptides share conserved regions near the putative cleavage sites. At a minimum, this molecule may be used as a standard in assays where molecular weight is being examined.

B. Functional Aspects

When the present application refers to the function of MCV type 1 or type 2 activity or "wild-type" activity, it is meant that the molecule in question has the ability to block the chemotactic response to human chemokines. Thus the molecules of the present invention act as antagonists of human chemokines and have an inhibitory effect on human hematopoeitic progenitor cells. Determination of which polypeptides possess this activity may be achieved using assays familiar to those of skill in the art. For example, transfer of genes encoding MCV type 1 or type 2 protein or variants thereof, into cells that are capable of responding to human chemokines will result in the inhibition chemotactic response to chemokines such as MIP1-A, or MCP, and hence will identify those molecules having MCV chemokine-like protein function.

For example, cell extracts may be assayed for by transfecting cells with the test cDNA in an appropriate vector and then assaying these cells for inhibition of chemotaxis as described in the examples. Assays for hematopoeitic progenitor cell colony formation are well known to those of skill in the art (Broxmeyer et al., 1990; 1993; 1995) and may be used to identify molecules with MCV type 1 and type 2 activity as described herein below.

C. Variants of MCV type 1 and Type 2 proteins

Amino acid sequence variants of the polypeptides can be substitutional, insertional or deletion variants. Deletion variants lack one or more residues of the native protein which are not essential for function or immunogenic activity, and are exemplified by the variants lacking a leader sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity, as discussed below. Table 1 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outline above, to engineer second generation molecules having many of the natural properties of MCV-type 1 and type 2 viral proteins, but with altered and even improved characteristics.

D. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of a immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. Fusion to a polypeptide that can be used for purification of the substrate-MCV chemokine-like viral protein complex would serve to isolated the natural receptor for these chemokine-like proteins for identification and analysis.

E. Purification of Proteins

It will be desirable to purify the chemokine-like viral proteins or variants thereof for use in the therapeutic applications disclosed herein and to generate antibodies as described herein below. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosarnine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

F. Synthetic Peptides

The present invention also describes smaller MCV-type 1 and type 2 related peptides for use in various embodiments of the present invention. Because of their relatively small size, the peptides of the invention can also be synthesized in solution or on a solid support in accordance with conventional techniques. Indeed, the full length proteins may also be synthesized using the methods described herein. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Short peptide sequences, or libraries of overlapping peptides, usually from about 6 up to about 35 to 50 amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

G. Antigen Compositions

The present invention also provides for the use of MCV type 1 and type 2 proteins or peptides as antigens for the immunization of animals relating to the production of antibodies. It is envisioned that either MCV type 1 and type 2 proteins, or portions thereof, will be coupled, bonded, bound, conjugated or chemically-linked to one or more agents via linkers, polylinkers or derivatized amino acids. This may be performed such that a bispecific or multivalent composition or vaccine is produced. It further is envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

IV. Nucleic Acids

The present invention also provides, in another embodiment, genes encoding MCV type 1 and type 2 proteins. The present invention identifies the gene for the chemokine like viral proteins from MCV, however, the present invention is not limited in scope to these genes, as one of ordinary skill in the art could, using the nucleic acids disclosed herein, readily identify related homologs in various other species.

In addition, it should be clear that the present invention is not limited to the specific nucleic acids disclosed herein. As discussed below, a "MCV type 1 gene or an MCV type 2 gene" may contain a variety of different bases and yet still produce a corresponding polypeptides that is functionally indistinguishable, and in some cases structurally, from the human and mouse genes disclosed herein.

Similarly, any reference to a nucleic acid should be read as encompassing a host cell containing that nucleic acid and, in some cases, capable of expressing the product of that nucleic acid. In addition to therapeutic considerations, cells expressing nucleic acids of the present invention may prove useful in the context of screening for agents that induce, repress, inhibit, augment, interfere with, block, abrogate, stimulate or enhance the function of the MCV chemokine-like viral proteins disclosed herein.

A. Nucleic Acids Encoding MCV Chemokine-like Viral Proteins

The gene disclosed in SEQ ID NO: 1 is the MCV type 2 gene of the present invention SEQ ID NO:3 discloses the MCV type 1 gene of the present invention. Nucleic acids according to the present invention may encode an entire MCV type 1 or type 2 gene, a domain of MCV type 1 or type 2 that expresses function capable of antagonizing human chemokine function or inhibiting the growth of hematopoietic progenitor cell proliferation, or any other fragment of the MCV types 1 or 2 sequences set forth herein. The nucleic acid may be derived from genomic DNA, i.e., cloned directly from the genome of a particular organism. In preferred embodiments, however, the nucleic acid would comprise complementary DNA (cDNA). Also contemplated is a cDNA plus a natural intron or an intron derived from another gene; such engineered molecules are sometime referred to as "mini-genes." At a minimum, these and other nucleic acids of the present invention may be used as molecular weight standards in, for example, gel electrophoresis.

The term "cDNA" is intended to refer to DNA prepared using messenger RNA (mRNA) as template. The advantage of using a cDNA, as opposed to genomic DNA or DNA polymerized from a genomic, non- or partially-processed RNA template, is that the cDNA primarily contains coding sequences of the corresponding protein. There may be times when the full or partial genomic sequence is preferred, such as where the non-coding regions are required for optimal expression or where non-coding regions such as introns are to be targeted in an antisense strategy.

It also is contemplated that a given MCV chemokine-like gene from a given species may be represented by natural variants that have slightly different nucleic acid sequences but, nonetheless, encode the same protein (see Table 1 below).

As used in this application, the term "a nucleic acid encoding an MCV chemokine-like protein" refers to a nucleic acid molecule that has been isolated free of total cellular nucleic acid. In preferred embodiments, the invention concerns a nucleic acid sequence essentially as set forth in SEQ ID NO:1 or SEQ ID NO:3. The term "as set forth SEQ ID NO:1 or SEQ ID NO:3" means that the nucleic acid sequence substantially corresponds to a portion of SEQ ID NO:1 or SEQ ID NO:3 respectively. The term "functionally equivalent codon" is used herein to refer to codons that encode the same amino acid, such as the six codons for arginine or serine (Table 1, below), and also refers to codons that encode biologically equivalent amino acids, as discussed in the following pages.

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Allowing for the degeneracy of the genetic code, sequences that have at least about 50%, usually at least about 60%, more usually about 70%, most usually about 80%, preferably at least about 90% and most preferably about 95% of nucleotides that are identical to the nucleotides of SEQ ID NO:1 or SEQ ID NO:3 will be sequences that are "as set forth in SEQ ID NO:1 or SEQ ID NO:3, respectively." Sequences that are essentially the same as those set forth in SEQ ID NO:1 or SEQ ID NO:3 may also be functionally defined as sequences that are capable of hybridizing to a nucleic acid segment containing the complement of SEQ ID NO:1 or SEQ ID NO:3, respectively under standard conditions.

The DNA segments of the present invention include those encoding biologically functional equivalent MCV type 1 or type 2 proteins and peptides, as described above. Such sequences may arise as a consequence of codon redundancy and amino acid functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques or may be introduced randomly and screened later for the desired function, as described below.

B. Oligonucleotide Probes and Primers

Naturally, the present invention also encompasses DNA segments that are complementary, or essentially complementary, to the sequence set forth in SEQ ID NO:1 or SEQ ID NO:3. Nucleic acid sequences that are "complementary" are those that are capable of base-pairing according to the standard Watson-Crick complementary rules. As used herein, the term "complementary sequences" means nucleic acid sequences that are substantially complementary, as may be assessed by the same nucleotide comparison set forth above, or as defined as being capable of hybridizing to the nucleic acid segment of SEQ ID NO:1 or SEQ ID NO:3 under relatively stringent conditions such as those described herein. Such sequences may encode the entire MCV type 1 or type 2 protein respectively or functional or non-functional fragments thereof.

Alternatively, the hybridizing segments may be shorter oligonucleotides. Sequences of 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that exemplary oligonucleotides of 8, 9, 10, 11, 12, 13, 14, 15, 16, 17, 18, 19, 20, 25, 30, 35, 40, 45, 50, 55, 60, 65, 70, 75, 80, 85, 90, 95, 100 or more base pairs will be used, although others are contemplated. Longer polynucleotides encoding 150, 160, 170, 180, 190, 200, 250, 270, 300 or 315 bases and longer are contemplated as well. Such oligonucleotides will find use, for example, as probes in Southern and Northern blots and as primers in amplification reactions.

Suitable hybridization conditions will be well known to those of skill in the art. In certain applications, for example, substitution of amino acids by site-directed mutagenesis, it is appreciated that lower stringency conditions are required. Under these conditions, hybridization may occur even though the sequences of probe and target strand are not perfectly complementary, but are mismatched at one or more positions. Conditions may be rendered less stringent by increasing salt concentration and decreasing temperature. For example, a medium stringency condition could be provided by about 0.1 to 0.25 M NaCl at temperatures of about 37° C. to about 55° C., while a low stringency condition could be provided by about 0.15 M to about 0.9 M salt, at temperatures ranging from about 20° C. to about 55° C. Thus, hybridization conditions can be readily manipulated, and thus will generally be a method of choice depending on the desired results.

In other embodiments, hybridization may be achieved under conditions of, for example, 50 mM Tris-HCl (pH 8.3), 75 mM KCl, 3 mM $MgCl_2$, 10 mM dithiothreitol, at temperatures between approximately 20° C. to about 37° C. Other hybridization conditions utilized could include approximately 10 mM Tris-HCl (pH 8.3), 50 mM KCl, 1.5 $\mu$M $MgCl_2$, at temperatures ranging from approximately 40° C. to about 72° C. Formamide and SDS also may be used to alter the hybridization conditions.

One method of using probes and primers of the present invention is in the search for genes related to MCV type 1 or type 2 or, more particularly, homologs of chemokine-like proteins from other species. Normally, the target DNA will be a genomic or cDNA library, although screening may involve analysis of RNA molecules. By varying the stringency of hybridization, and the region of the probe, different degrees of homology may be discovered.

Another way of exploiting probes and primers of the present invention is in site-directed, or site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

C. Antisense Constructs

In some cases, it may be necessary to abrogate the function of MCV viral proteins. For example it has been shown that the MCV type 1 and type 2 viral proteins are likely expressed in proliferative lesions of immunocompromised individuals. The Hence it will be useful to make these lesions amenable to host immune system attack by removing the function of the MCV chemokine-like proteins. Antisense treatments are one way of addressing this situation. Antisense technology also may be used to "knock-out" function of MCV types 1 and 2 protein in the development of cell lines for research, diagnostic and screening purposes.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

D. Ribozymes

Another approach for addressing the "dominant negative" phenotype is through the use of ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

E. Vectorsfor Cloning, Gene Transfer and Expression

Within certain embodiments expression vectors are employed to express the MCV chemokine like viral polypeptide products, which can then be purified and, for example, be used to vaccinate animals to generate antisera or monoclonal antibody with which further studies may be conducted. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

(i) Regulatory Elements

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several elements/promoters which may be employed, in the context of the present invention, to regulate the expression of the gene of interest. This list is not intended to be exhaustive of all the possible elements involved in the promotion of gene expression but, merely, to be exemplary thereof.

Neuron-specific gene expression has been extensively studied and recently reviewed (Twyman and Jones, 1995). For example, brain derived neurotrophic factor has four promoters that direct expression to the brain. The promoters for CaII, GAP-43, NaII NGF receptor and the neurofilament gene expression are examples of a pan-neural promoters, the skilled artisan is referred to Twyman and Jones (1995) and the references therein for further detail on these and other neuron specific promoter.

Several inducible promoter systems are available for production of expression constructs of the present invention. The ecdysone system (Invitrogen, Carlsbad, Calif.) is one such system. This system is designed to allow regulated expression of a gene of interest in mammalian cells. It consists of a tightly regulated expression mechanism that allows virtually no basal level expression of the transgene, but over 200-fold inducibility. The system is based on the heterodimeric ecdysone receptor of Drosophila, and when ecdysone or an analog such as muristerone A binds to the receptor, the receptor activates a promoter to turn on expression of the downstream transgene high levels of mRNA transcripts are attained. In this system, both monomers of the heterodimeric receptor are constitutively expressed from one vector, whereas the ecdysone-responsive promoter which drives expression of the gene of interest is on another plasmid. Engineering of this type of system into the gene transfer vector of interest would therefore be useful. Cotransfection of plasmids containing the gene of interest and the receptor monomers in the producer cell line would then allow for the production of the gene transfer vector without expression of a potentially toxic transgene. At the appropriate time, expression of the transgene could be activated with ecdysone or muristeron A.

Another inducible system that would be useful is the Tet-Off™ or Tet-On™ system (Clontech, Palo Alto, Calif.) originally developed by Gossen and Bujard (Gossen and Bujard, 1992; Gossen et al., 1995). This system also allows high levels of gene expression to be regulated in response to tetracycline or tetracycline derivatives such as doxycycline. In the Tet-On™ system, gene expression is turned on in the presence of doxycycline, whereas in the Tet-Off™ system, gene expression is turned on in the absence of doxycycline. These systems are based on two regulatory elements derived from the tetracycline resistance operon of E. coli, i.e., the tetracycline operator sequence to which the tetracycline repressor binds, and the tetracycline repressor protein. The gene of interest is cloned into a plasmid behind a promoter that has tetracycline-responsive elements present in it. A second plasmid contains a regulatory element called the tetracycline-controlled transactivator, which is composed, in the Tet-Off™ system, of the VP16 domain from the herpes simplex virus and the wild-type tetracycline repressor. Thus, in the absence of doxycycline, transcription is constitutively on. In the Tet-On™ system, the tetracycline repressor is not wild type and in the presence of doxycycline activates transcription. For gene transfer vector production, the Tet-Off™ system would be preferable so that the producer cells could be grown in the presence of tetracycline or doxycycline and prevent expression of a potentially toxic transgene, but when the vector is introduced to the patient, the gene expression would be constitutively on.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Below is a list of viral promoters, cellular promoters/enhancers and inducible promoters/enhancers that could be used in combination with the nucleic acid encoding a gene of interest in an expression construct (Table 2 and Table 3). Additionally, any promoter/enhancer combination (as per the Eukaryotic Promoter Data Base EPDB) could also be used to drive expression of the gene. Eukaryotic cells can support cytoplasmic transcription from certain bacterial promoters if the appropriate bacterial polymerase is provided, either as part of the delivery complex or as an additional genetic expression construct.

TABLE 2

| ENHANCER/PROMOTER |
| --- |
| Immunoglobulin Heavy Chain |
| Immunoglobulin Light Chain |
| T-Cell Receptor |
| HLADQα and DQβ |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| e-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |

TABLE 2-continued

| ENHANCER/PROMOTER |
| --- |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

TABLE 3

| Element | Inducer |
| --- | --- |
| MT II | Phorbol Ester (TPA) |
| | Heavy metals |
| MMTV (mouse mammary tumor virus) | Glucocorticoids |
| β-Interferon | poly(rI)X |
| | poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |
| GRP78 Gene | A23187 |
| α-2-Macroglobulin | IL-6 |
| Vimentin | Serum |
| MHC Class I Gene H-2kB | Interferon |
| HSP70 | E1a, SV40 Large T Antigen |
| Proliferin | Phorbol Ester-TPA |
| Tumor Necrosis Factor | FMA |
| Thyroid Stimulating Hormone α Gene | Thyroid Hormone |
| Insulin E Box | Glucose |

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

(ii) Selectable Markers

In certain embodiments of the invention, the cells contain nucleic acid constructs of the present invention, a cell may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

(iii) Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picanovirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

(iv) Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Both ends of the viral genome contain 100–200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP, (located at 16.8 m.u.) is particularly efficient during the late phase of infection, and all the mRNA's issued from this promoter possess a 5'-tripartite leader (TPL) sequence which makes them preferred mRNA's for translation.

Generation and propagation of the current adenovirus vectors, which may be replication deficient, depend on a unique helper cell line, designated 293, which was transformed from human embryonic kidney cells by Ad$\gamma$ DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Mulligan, 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Recently, Racher et al., (1995) disclosed improved methods for culturing 293 cells and propagating adenovirus. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Other than the requirement that the adenovirus vector be replication defective, or at least conditionally defective, the nature of the adenovirus vector is not believed to be crucial to the successful practice of the invention. The adenovirus may be of any of the 42 different known serotypes or subgroups A–F. Adenovirus type 5 of subgroup C is the preferred starting material in order to obtain the conditional replication-defective adenovirus vector for use in the present invention. This is because Adenovirus type 5 is a human adenovirus about which a great deal of biochemical and genetic information is known, and it has historically been used for most constructions employing adenovirus as a vector.

As stated above, the typical vector according to the present invention is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical to the invention. The polynucleotide encoding the gene of interest may also be inserted in lieu of the deleted E3 region in E3 replacement vectors as described by Karlsson et al., (1986) or in the E4 region where a helper cell line or helper virus complements the E4 defect.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact-sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Adeno-associated viruses (AAVs) utilizes a linear, single-stranded DNA of about 4700 base pairs. Inverted terminal repeats flank the genome. Two genes are present within the genome, giving rise to a number of distinct gene products. The first, the cap gene, produces three different virion proteins (VP), designated VP-1, VP-2 and VP-3. The second, the rep gene, encodes four non-structural proteins (NS). One or more of these rep gene products is responsible for transactivating AAV transcription.

The three promoters in AAV are designated by their location, in map units, in the genome. These are, from left to right, p5, p19 and p40. Transcription gives rise to six transcripts, two initiated at each of three promoters, with one of each pair being spliced. The splice site, derived from map units 42–46, is the same for each transcript. The four non-structural proteins apparently are derived from the longer of the transcripts, and three virion proteins all arise from the smallest transcript.

AAV is not associated with any pathological state in humans. Interestingly, for efficient replication, AAV requires "helping" functions from viruses such as herpes simplex virus I and II, cytomegalovirus, pseudorabies virus and, of course, adenovirus. The best characterized of the helpers is adenovirus, and many "early" functions for this virus have been shown to assist with AAV replication. Low level expression of AAV rep proteins is believed to hold AAV structural expression in check, and helper virus infection is thought to remove this block.

The terminal repeats of the AAV vector can be obtained by restriction endonuclease digestion of AAV or a plasmid such as psub201, which contains a modified AAV genome (Samulski et al. 1987), or by other methods known to the skilled artisan, including but not limited to chemical or enzymatic synthesis of the terminal repeats based upon the published sequence of AAV. The ordinarily skilled artisan can determine, by well-known methods such as deletion analysis, the minimum sequence or part of the AAV ITRs which is required to allow function, i.e., stable and site-specific integration. The ordinarily skilled artisan also can determine which minor modifications of the sequence can be tolerated while maintaining the ability of the terminal repeats to direct stable, site-specific integration.

AAV-based vectors have proven to be safe and effective vehicle for gene delivery in vitro, and these vectors are now being developed and tested in pre-clinical and clinical stages for a wide range of applications in potential gene therapy, both ex vivo and in vivo (Carter and Flotte, 1996; Chatterjee et al., 1995; Ferrari et al., 1996; Fisher et al., 1996; Flotte et al., 1993; Goodman et al., 1994; Kaplitt et al., 1994; 1996; Kessler et al., 1996; Koeberl et al., 1997; Mizukami et al., 1996; Xiao et al., 1996).

AAV-mediated efficient gene transfer and expression in the lung has led to clinical trials for the treatment of cystic fibrosis (Carter and Flotte, 1996; Flotte et al., 1993). Similarly, the prospects for treatment of muscular dystrophy by AAV-mediated gene delivery of the dystrophin gene to skeletal muscle, of Parkinson's disease by tyrosine hydroxylase gene delivery to the brain, of hemophilia B by Factor IX gene delivery to the liver, and potentially of myocardial infarction by vascular endothelial growth factor gene to the heart, appear promising since AAV-mediated transgene expression in these organs has recently been shown to be highly efficient (Fisher et al., 1996; Flotte et al., 1993; Kaplitt et al., 1994; 1996; Koeberl et al., 1997; McCown et al., 1996; Ping et al., 1996; Xiao et al., 1996).

Other viral vectors may be employed as expression constructs in the present invention. Vectors derived from viruses such as vaccinia virus (Ridgeway, 1988; Baichwal and Sugden, 1986; Coupar et al., 1988) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

Lentiviruses can also be used as vectors in the present application. In addition to the long-term expression of the transgene provided by all retroviral vectors, lentiviruses present the opportunity to transduce nondividing cells and potentially achieve regulated expression. The development of lentiviral vectors requires the design of transfer vectors to ferry the transgene with efficient encapsidation of the transgene RNA and with full expression capability, and of a packaging vector to provide packaging machinery in trans but without helper virus production. For both vectors, a knowledge of packaging signal is required-the signal to be included in the transfer vector but excluded from the packaging vector. Exemplary human lentiviruses are human immunodeficiency virus type 1 and type 2 (HIV-1 and HIV-2). HIV-2 is likely better suited for gene transfer than HIV-1 as it is less pathogenic and thus safer during design and production; its desirable nuclear import and undesirable cell-cycle arrest functions are segregated on two separate genes (Arya et al., 1998; Blomer et al., 1997).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1 980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a 5 liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations. Antibodies are and their uses are discussed further, below.

V. Generating Antibodies Reactive With MCV Chemokine-Like Viral Proteins

In another aspect, the present invention contemplates an antibody that is immunoreactive with a chemokine-like molecule of the present invention, or any portion thereof. An antibody can be a polyclonal or a monoclonal antibody. In a preferred embodiment, an antibody is a monoclonal antibody. Means for preparing and characterizing antibodies are well known in the art (see, e.g., Howell and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of the compounds of the present invention can be used to immunize one or more experimental animals, such as a rabbit or mouse, which will then proceed to produce specific antibodies against the compounds of the present invention. Polyclonal antisera may be obtained, after allowing time for antibody generation, simply by bleeding the animal and preparing serum samples from the whole blood.

It is proposed that the monoclonal antibodies of the present invention will find useful application in standard immunochemical procedures, such as ELISA and Western blot methods and in immunohistochemical procedures such as tissue staining, as well as in other procedures which may utilize antibodies specific to an MCV type 1 or type 2-related antigen epitopes. In addition antibodies identified by the present application may be useful in the therapeutic treatments of MCV infection.

In general, both polyclonal and monoclonal antibodies against MCV types 1 and 2 may be used in a variety of embodiments. For example, they may be employed in antibody cloning protocols to obtain cDNAs or genes encoding other chemokine-like proteins. They may also be used in inhibition studies to analyze the effects of MCV type 1 or Type 2 related peptides in cells or animals. Anti-MCV type 1 and type 2 antibodies will also be useful in immunolocalization studies to analyze the distribution of MCV chemokine-like proteins during various cellular events, for example, to determine the cellular or tissue-specific distribution of MCV types 1 and 2 polypeptides under different points in the cell infection. A particularly useful application of such antibodies is in purifying native or recombinant MCV chemokine-like proteins, for example, using an antibody affinity column. The operation of all such immunological techniques will be known to those of skill in the art in light of the present disclosure.

Means for preparing and characterizing antibodies are well known in the art (see, e.g., Harlow and Lane, 1988; incorporated herein by reference). More specific examples of monoclonal antibody preparation are give in the examples below.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified MCV type 1 or type 2 protein, polypeptide or peptide or cell expressing high levels of MCV chemokine-like protein. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986). For example, where the immunized animal is a mouse, one may use P3-X63/Ag8, P3-X63-Ag8.653, NS1/1.Ag 4 1, Sp210-Ag14, FO, NSO/U, MPC-11, MPC 11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with mycloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods is also appropriate (Goding, 1986).

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g, hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

Antibodies of the present invention can be used in characterizing the MCV type 1 and type 2 content of healthy and diseased tissues, through techniques such as ELISAs and Western blotting. This may provide a screen for the presence or absence of MCV infection in immunocompromised individuals.

The use of antibodies of the present invention, in an ELISA assay is also contemplated. For example, anti-MCV type 1 and type 2 antibodies are immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface.

After binding of antibody to the well, coating with a non-reactive material to reduce background, and washing to remove unbound material, the immobilizing surface is contacted with the sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for chemokine-like viral protein that differs the first antibody. Appropriate conditions preferably include diluting the sample with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

To provide a detecting means, the second antibody will preferably have an associated enzyme that will generate a color development upon incubating with an appropriate chromogenic substrate. Thus, for example, one will desire to contact and incubate the second antibody-bound surface with a urease or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

The preceding format may be altered by first binding the sample to the assay plate. Then, primary antibody is incubated with the assay plate, followed by detecting of bound primary antibody using a labeled second antibody with specificity for the primary antibody.

The antibody compositions of the present invention will find great use in immunoblot or Western blot analysis. The antibodies may be used as high-affmity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

VI. Methods for Screening Active Compounds

The present invention also contemplates the use of MCV viral chemokine-like proteins and active fragments, and nucleic acids coding therefor, in the screening of compounds for activity in either stimulating MCV chemokine-like activity where it is necessary to decrease the function of human chemokines, or blocking the effect of a MCV viral chemokine-like viral proteins in MCV infection. These assays may make use of a variety of different formats and may depend on the kind of "activity" for which the screen is being conducted. Contemplated functional "read-outs" include chemotaxis assays and hematopoeitic progenitor cell proliferation assays, as well as ligand (e.g. receptor-mediated $Ca^{2+}$ flux), receptor or other binding partner by a compound, inhibition or stimulation of cell-to-cell signaling, growth, or cell migration.

A. In Vitro Assays

In one embodiment, the invention is to be applied for the screening of compounds that bind to the chemokine-like MCV viral protein molecule or fragment thereof. The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of MCV type 1 or type 2 to a natural or artificial substrate or binding partner. Competitive binding assays can be performed in which one of the agents (MCV type 1 or type 2, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with the MCV chemokine-like polypeptide and washed. Bound polypeptide is detected by various methods.

Purified MCV type 1 or type 2 protein can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the protein active region to a solid phase.

Various cell lines containing wild-type or natural or engineered mutations in MCV chemokine-like viral proteins can be used to study various functional attributes of the proteins and how a candidate compound affects these attributes. Methods for engineering mutations are described elsewhere in this document, as are naturally-occurring mutations in MCV type 1 and type 2 proteins that lead to, contribute to and/or otherwise cause a detrimental effect in MCV infection. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of MCV type 1 or type 2 protein, or related pathways, may be explored. This may involve assays such as those for protein expression, enzyme function, substrate utilization, phosphorylation states of various molecules including chemokine-like MCV proteins, cAMP levels, mRNA expression (including differential display of whole cell or polyA RNA) and others.

B. Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules (Hodgson J. (1991) Bio/Technology 9:19–21). In one approach, one would generate a three-dimensional structure the protein of interest or a fragment thereof. This could be accomplished by x-ray crystallograph, computer modeling or by a combination of both approaches. Useful examples of rational drug design may include molecules which have improved activity or stability as shown by Braxton S. and Wells J. A. (1992 Biochemistry 31:7796–7801) or which act as inhibitors, agonists, or antagonists of native peptides as shown by Athauda S. B. et al (1993 J Biochem 113:742–746). An alternative approach, "alanine scan," involves the random replacement of residues throughout molecule with alanine, and the resulting affect on function determined.

It also is possible to isolate a target-specific antibody, selected by a functional assay, and then solve its crystal structure, where the target is a chemokine-like MCV viral protein of the present invention. In principle, this approach yields a pharmacore upon which subsequent drug design can be based. It is possible to bypass protein crystallograph altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved MCV type 1 and type 2 activity or which act as stimulators, inhibitors, agonists, antagonists of MCV type 1 and type 2 proteins or molecules affected by such proteins i.e. human chemokines. By virtue of the availability of cloned MCV type 1 and type 2 chemokine-like sequences, sufficient amounts of polypeptide can be produced to perform crystallographic studies. In addition, knowledge of the polypeptide sequences permits computer employed predictions of structure-function relationships.

C. Identification of MCV Viral Protein Receptors

Purified MCV viral protein composition of the present invention will be useful for the characterization and purification of specific cell surface receptors and other binding molecules. Cells which respond to the MCV viral proteins by blocking the chemotaxic response of the natural chemokines or other specific responses may likely express a receptor to which MCV chemokine-like proteins bind. Radioactive labels may be incorporated into chemokine antagonists of the present invention by various methods known in the art. A preferred embodiment is the labeling of primary amino groups in the chemokine-like viral proteins with $^{125}$I Bolton-Hunter reagent (Bolton, A. E. and Hunter, W. M. (1973) Biochem J 133: 529), which has been used to label chemokines without concomitant loss of biological activity (Hebert C. A. et al (1991) J Biol Chem 266: 18989; McColl S. et al (1993) J Immunol 150:4550–4555). Receptor-bearing cells are incubated with labeled chemokine antagonist proteins of the present invention. The cells are then washed to removed unbound protein, and receptor-bound MCV chemokine-like viral protein is quantified. The data obtained using different concentrations of MCV type 1 and type 2 proteins are used to calculate values for the number and affinity of receptors.

Labeled MCV type 1 or type 2 proteins will be useful as reagents for the purification of specific receptor molecules. In one embodiment of affinity purification, the MCV type 1 or type 2 protein is covalently coupled to a chromatography column. Receptor-bearing cells are extracted, and the extract is passed over the column. The receptor binds to the column by virtue of its biological affinity for the protein. The receptor is recovered from the column and subjected to N-terminal protein sequencing. This amino acid sequence is then used to design degenerate oligonucleotide probes for cloning the receptor gene.

In an alternate method, expression cloning, mRNA is obtained from receptor-bearing cells and made into a cDNA expression library. The library is transfected into a population of cells, and those cells in the population which express the receptor are selected using fluorescently labeled chemokine-like viral protein. The receptor is identified by recovering and sequencing recombinant DNA from highly labeled cells.

In yet another alternate method, antibodies are raised against the surface of receptor-bearing cells, specifically monoclonal antibodies. The monoclonal antibodies are screened to identify those which inhibit the binding of labeled chemokine-like proteins of the present invention. These monoclonal antibodies are then used in affinity purification or expression cloning of the receptor.

Soluble receptors or other soluble binding molecules may also be identified in a similar manner. Labeled chemokine-like proteins of the present invention are incubated with extracts or other appropriate materials derived from inflamed tissue. After incubation, MCV type 1 or type 2 complexes larger than the size of purified MCV type 1 or type 2 respectively are identified by a sizing technique such as size exclusion chromatography or density gradient centrifugation and are purified by methods known in the art. The soluble receptors or binding protein(s) are subjected to N-terminal sequencing to obtain information sufficient for database identification, if the soluble protein is known, or cloning, if the soluble protein is unknown.

VII. Methods of Treatment using MCV Chemokine-like Viral Proteins

The present invention also involves, in certain embodiments, the treatment of various disease states. The types of abnormalities that may be treated, according to the present invention, is limited only by the involvement of MCV chemokine-like viral proteins. By involvement, it is meant that the MCV chemokine-like viral proteins may be present, and producing a detrimental effect, in for example, MCV infections, and need to be deleted, abrogated or otherwise inhibited such that the immune response of the host animal may be facilitated. In other embodiments, it will be useful to supply MCV chemokine-like viral proteins in order to antagonize the action of natural chemokines and prevent the host's immune response, such as in a variety of inflammatory and allergenic responses, protect certain non-target cells from the deleterious effects of chemotherapy, as well as to inhibit HIV entry into target cells. These circumstances and methods of effecting such treatments are discussed herein below.

A. Types ofDiseased States Treated (i) Treatment of MCV Infection

As stated above, the composition of the present invention, in one embodiment, will be useful in the treatment of MCV infection. Such infection typically is responsible for the benign proliferative lesions of the skin seen in normal and immunocompromised individuals. MCV is the sole member of the genus Molluscipoxvirus and appears to have human-restricted host range. MCV infection occurs worldwide as a contact disease in children or as a sexually transmitted disease in adults. In children and teenagers the lesions appear n the trunk, limbs and face (Fenner and Nakano, 1988; Porter et al., 1992). Infection is usually transmitted by direct or indirect skin contact, such as among wrestlers, or in public baths and pools. As a sexually transmitted disease, the lesions are mostly on the lower abdominal wall, pubis, inner thighs and genitalia.

Lesions are pearly, flesh-colored, raised, firm, umbilicated nodules of about 4 cm in diameter. The lesions disseminate by autoinoculation and severe dissemination has been noted in immunocompromised individuals particularly AIDS patients. Multiple lesions may become confluent forming a single disfiguring plaque. From the results of the present invention it would appear that such lesions escape host immune attack by producing the viral chemokine-like proteins of the present invention which prevent the action of the natural chemokines in the human host. Thus in order to treat such lesions it will be necessary to inhibit, abrogate or otherwise overcome the effect of the MCV chemokine-like viral proteins. Such treatments may be gene based therapies where the expression of such proteins is inhibited by the use of antisense or ribozyme constructs. Alternatively, the present disclosure teaches the isolation of inhibitors of MCV action, the application of such inhibitors in pharmacological preparations will aid in the treating such lesions. In other embodiments, combinations of gene therapeutic and pharmacological agents will prove useful. Of course it would be desirable to completely abolish the lesions, however, any decrease in the size, number, or rate of proliferation of such lesions will be indicative of the compositions of the present invention being useful. Such compositions may also be administered prophylactically in individual suspected of having an MCV infection prior to the manifestation of the lesions.

(ii) Treatment of Inflammatory Response

In certain embodiments, the compositions of the present invention may be employed to prevent the host's immune response, for example, in circumstances where the native chemokines are overexpressed or inflammation needs to be controlled. In these instances, it will be necessary to enhance, add, increase or otherwise stimulate the MCV viral protein activity. Thus, it is contemplated that a wide variety of conditions may be treated using MCV chemokine-like therapy, including a plethora of allergic and autoimmune responses, including for example, asthma, Hodgkins disease, inflamed adenoids, tonsilitis, Epstein-Barr virus, pneumonia, myocarditis, rheumatoid arthristis, that are characterized by chemotactic responses to $\beta$ chemokines such as MCP, MIP-1$\alpha$, RANTES and the like.

Thus, the chemokine-like MCV viral compositions of the present invention may be used to treat conditions in which a chemokine-mediated inflammation has occurred or will occur. Such conditions may include delayed hypersensitivity reactions, inflammations such as inflamed adenoid, tonsilitis, Epstein-Barr virus, Hodgkin's disease, various neoplasms or nonspecific pharyngitis. In particular embodiments, the compositions of the present invention may be used in the treatment of mammals to control the amount or activity of an inflammatory cytokine, so as to alter the consequences of such presence or activity. Hence, the compositions may be used treat or avert the adverse consequences of invasive, spontaneous or idiopathic pathological states.

Antibodies and drugs that modulate the production or activity of the inflammatory cytokine as identified herein may possess certain therapeutic applications and may thus be utilized for the purpose of treating the effects attributable to the action of the inflammatory chemokines, such as inflammation and fever.

It is further contemplated that liver conditions or diseases which activates leukocytes, particularly monocytes and macrophages, and precipitates permanent damage may be treatable with the chemokine-like viral compositions of the present invention. Similarly treatable conditions or diseases of the pituitary can be diagnosed by specific testing, which should be performed for patients with adenoma or multiple endocrine neoplasia, as well as other genetic or invasive conditions that activate cells which may destroy or compromise the function of the pituitary gland.

In a particular embodiment, it has known that chemokines play a central role in transplant rejection as described herein above (Grandaliano et al., 1997; Pattison et al., 1994; 1996). Thus it is contemplated that the compositions of the present invention may also be administered to recipients of organ transplants in amounts effective to reduce the chemokine mediated immune attack of transplant.

(iii) Protection of Cells Against Chemotherapy

A major disadvantage to the use of chemo- and radio-therapies in the treatment of malignant conditions such as cancer is that such treatments compromise the bone marrow cells of the individual to which such therapy is being administered. Cells of the bone marrow are rapidly growing cells and are killed by the chemo and radiotherapies designed to kill malignant cells. To date bone marrow transplantation (BMT), is used in humans to replace these bone marrow cells lost to such chemo- and radiotherapy. BMT for the treatment of patients with a variety of malignancies and disorders is possible if a suitable donor may be located. This is at best impractical and often impossible. Even if a suitable donor can be found complications with graft rejection and graft versus host disease are many-fold, and include diarrhea, anorexia, nausea and vomiting as well as malabsorption, abdominal pain ileus and ascites formation.

A major advantage of the present invention is that the growth of the hematopoeitic cells may be inhibited by the MCV chemokine-like proteins of the present invention, as shown in Example 5. Thus, when an individual is receiving chemo- or radiation therapy, about to receive such therapy, or is candidate for future therapy involving radio or chemotherapeutic, the bone marrow cells of the individual may be treated with the compositions of the present invention to prevent or slow their growth such that the chemo and radiotherapeutic agents will not kill these cells.

(iv) Use of Chemokine-like MCV Viral Proteins to Prevent HIV Infection

Chemokines have also been implied in the blocking of HIV entry into the lymphocyte presumably by preferentially binding to the C—C chemokine receptor which has been show to be an HIV co-receptor. The compositions of the present invention may be used to preferentially bind to the C—C receptors and prevent the binding and entry of the HIV infective entity.

B. Methods ofEffecting Treatment (i) Genetic Based Therapies

One of the therapeutic embodiments contemplated by the present inventors is the intervention, at the molecular level, in the events involved in the human inflammatory response. Specifically, the present inventors intend to provide, to a host cell, an expression construct capable of providing a chemokine-like viral protein to that cell. Because the nucleic acids of the present invention have been shown to block the chemotactic response to the human chemokine MIP-1α, any of these nucleic acids could be used in human therapy, as could any of the gene sequence variants discussed above which would encode the same, or a biologically equivalent polypeptide. The lengthy discussion of expression vectors and the genetic elements employed therein is incorporated into this section by reference. Particularly preferred expression vectors are viral vectors such as adenovirus, adeno-associated virus, herpesvirus, vaccinia virus and retrovirus. Also preferred is liposomally-encapsulated expression vector.

Those of skill in the art are well aware of how to apply gene delivery to in vivo and ex vivo situations. For viral vectors, one generally will prepare a viral vector stock. Depending on the kind of virus and the titer attainable, one will deliver $1 \times 10^4$, $1 \times 10^5$, $1 \times 10^6$, $1 \times 10^7$, $1 \times 10^8$, $1 \times 10^9$, $1 \times 10^{10}$, $1 \times 10^{11}$ or $1 \times 10^{12}$ infectious particles to the patient. Similar figures may be extrapolated for liposomal or other non-viral formulations by comparing relative uptake efficiencies. Formulation as a pharmaceutically acceptable composition is discussed below.

(ii) Immunotherapies

Immunotherapeutics, generally, rely on the use of immune effector cells and molecules to target and destroy invasive cells. The immune effector may be, for example, an anti-MCV chemokine-like antibody specific for use against MCV infections. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a cell target. Various effector cells include cytotoxic T cells and NK cells.

According to the present invention, it is unlikely that MCV viral proteins disclosed herein could serve as a target for an immune effector given that (i) it is unlikely to be expressed on the surface of the cell and (ii) that the presence of these proteins effects immune escape. However, it is possible that particular forms of MCV viral proteins may be targeted by immunotherapy, either using antibodies, antibody conjugates or immune effector cells.

A more likely scenario is that immunotherapy could be used as part of a combined therapy, in conjunction with MCV viral protein-targeted gene therapy. The general approach for combined therapy is discussed below. Generally, the cell must bear some marker that is amenable to targeting, ie., is not present on the majority of other cells. Many markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

(iii) Protein Therapy

Another therapy approach is the provision, to a subject, of an MCV chemokine-like viral polypeptide, active fragments, synthetic peptides, mimetics or other analogs thereof in order to combat the human chemokine-mediated inflammatory disease. The protein may be produced by recombinant expression means or, if small enough, generated by an automated peptide synthesizer. Formulations would be selected based on the route of administration and purpose including, but not limited to, liposomal formulations and classic pharmaceutical preparations.

(iv) Combination Therapy

The present section contemplates the use of the MCV chemokine-like viral protein based therapies discussed above in combination with other therapies. One goal of the present invention is to find ways to improve the antiviral therapy for such individuals with MCV infection. In other circumstances, there is a wide variety of inflammatory diseases that are mediated by the action of chemokines. The present invention for the first time provides viral chemokine compositions that blocks the chemotactic activity of natural chemokines. The present invention provides therapeutic compositions that may be used in combination with conventional antiviral and anti-inflammatory agents in order to alleviate the diseased states described herein.

In one embodiment, to effect a therapeutic outcome in cells, using the methods and compositions of the present invention, one would generally contact a "target" cell with a protein or an expression construct encoding the protein in an amount effective to inhibit human chemokine response, inhibit MIP-1α activity, or inhibit chemokine-mediated inflammation. This may be combined with compositions comprising other agents effective in the treatment of inflammatory response. These compositions would be provided in a combined amount effective to decrease the inflammatory response, decrease chemotaxis in said target cell or inhibit proliferation hematopoeitic progenitor cells.

In other alternative embodiments, the present invention contemplates abrogating or inhibiting the formation of lesions that occur as a result of MCV infection. In such cases, a practitioner of skill in the art may provide antisense expression constructs in order to decrease the expression of the MCV viral protein in the lesions. Again these compositions may be provided in combination with conventional antiviral agents known to those of skill in that art. Alternatively, the present invention further contemplates the provision of candidate antiviral and anti-inflammatory substances isolated using the methodology set forth herein above.

In yet another embodiment, the compositions of the present invention may be used in a method of protecting bone marrow cells from chemotherapy comprising administering a composition comprising a chemokine-like MCV viral protein in an effective to prevent the proliferation of said cells. These compositions will be administered in combination with conventional chemotherapy to treat cancer but protect the bone marrow cells of the individual. Agents or factors suitable for use in such a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

The skilled artisan is directed to "Remington's Pharmaceutical Sciences" 15th Edition, for disclosure pertaining to chemotherapeutic compounds, as well as antiviral and anti-inflammatory agents for use in combination with the disclosed invention. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The process of contacting a cell with the combined therapeutics of the present invention may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from minutes to weeks. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 hours of each other and, more preferably, within about 6–12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either expression construct or the other agent will be desired. Various combinations may be employed, where the expression construct is "A" and the other agent is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

The inventors propose that the regional delivery of the therapeutic expression constructs to patients will be a very efficient method for delivering a therapeutically effective gene to counteract the clinical disease. Similarly, the chemo- or radiotherapy may be directed to a particular, affected region of the subjects body. Alternatively, systemic delivery of expression construct and/or the agent may be appropriate in certain circumstances.

VIII. Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

XI. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Materials and Methods

Extraction of DNA. Specimens were collected by curettage from patients who were being treated for multiple molluscum lesions. The extracted lesion contents were minced with a scalpel blade and incubated overnight in a solution containing protease K (200 µg/ml) and 1% SDS. The mixture was then extracted with phenol and chloroform:isoamyl alcohol (24:1) and the DNA was precipitated with ethanol. Determination of MCV type was done by restriction endonuclease digestion of viral DNA as previously described (Fife et al., 1996).

Cloning. PCR™ primers specific for the MC148R gene were synthesized on Applied Biosystems oligonucleotide synthesizer. The 5' primer used was CCAAGAGGAC-GAGCTAA (SEQ ID NO:8), and the 3' primer was GTTCTCCTGCTCCATGACGA (SEQ ID NO:9). PCR™ reaction were carried out in the Perkin-Elmer GeneAmp PCR™ System 9600 (Perkin Elmer, Norwalk, CT) using 35 cycles of 3 temperatures of 94° C., 55° C., and 72° C. for 1 minute each. The product obtained was cloned into the cloning vector, PCR™ 3.1 (Invitrogen, San Diego, Calif.) using standard procedures specified by the manufacturer. Sequencing of the clone was carried out on the ABI Prism sequencer to confirm the predicted nucleotide sequence of the cloned segment. The cloned insert was then excised by BamH1/Sma1 double digestion and ligated into the baculovirus expression vector, pVL 1392 (Pharmingen, San Diego, Calif.).

Protein Production and Purification. The pVL vector with the MC148R gene was cotransfected with Baculovirus DNA containing a lethal deletion into Sf9 insect cells according to the manufacturer's directions. Resulting recombinant virus was amplified twice to high titer and Sf9 cells were infected in spinner flasks using protein free medium. Medium was then clarified by centrifugation at 10,000×g and passed over a heparin-sepharose column (Pharmacia, Piscataway, N.J.). Heparin binding proteins were eluted with a gradient of KCl. Only the initial fraction (0.25 M KCl) contained the protein of interest as judged by SDS-PAGE. High molecular weight contaminants were removed by centrifugation through a Centricon-30 column (Amicon, Beverly, Mass.) and the fraction passing through the membrane was collected and used in functional assays. Protein was quantified using the Bradford assay (Pierce, Rockford, Ill.).

Chemotaxis Assays. Twenty mL of venous blood was collected from healthy volunteers in 10 cc heparinized tubes. Blood was mixed 1:1 with phosphate buffered saline and 10 cc of Histopaque (Sigma, St. Louis, Mo.) was underlayed. Tubes were centrifuged at 400×g for 25 min. The band of mononuclear cells at the interface was collected and washed twice with PBS. Cells were resuspended in Dulbecco's minimal essential medium (Gibco BRL, Gaithersburg, Md.) with antibiotics at a density of $10^6$/ml. Bovine Serum albumin was added to cells as described previously (Martinet, 1994).

Chemotaxis was assayed using a modification of the method described by Boyden (Boyden, 1962; Keller, 1972). One hundred mL of the mononuclear cell suspension was added to each Transwell insert (Costar, Cambridge, Mass.). Dulbecco's minimal essential medium with antibiotics, 0.2 mg/ml bovine serum albumin and the protein to be tested were placed in the bottom wells of a 24 well plate. All samples were done in triplicate, and at least 2 studies for each protein were performed. Inserts were placed in the 24 well plate and incubated at 37° C. in 5% $CO_2$ for 90 minutes. At the end on the incubation, inserts were removed, the top of the insert was scraped with a rubber policeman to remove adherent cells and the filters were stained with Wright-Giemsa stain. Cells adherent to the bottom of the filter were counted under 3 high power fields, and cells that had migrated to the bottom of the 24 well plate were counted under 3 high power fields as well. These two values were summed and expressed as total migrating cells (Keller, 1972). For presentation of results, the total migrating cells in each study were expressed as a percentage of the positive control for that study (10 ng of MIP-1α obtained from Collaborative Biomedical Products, Bedford, Mass.) and the results for different studies were averaged.

Hematopoietic Progenitor Assays. Hematopoietic colony formation assays were performed as described previously (Broxmeyer et al., 1995; Broxmeyer et al., 1993; Broxmeyer et al., 1990). Volunteer human bone marrow cells were collected from donors after obtaining informed consent. Low density human marrow cells at $5 \times 10^4$/ml were plated in 1% methylcellulose in Iscove's modified medium supplemented with 30% fetal calf serum, recombinant human (rHu) erythropoietin (1 U/ml), rHu interleukin-3 (100 U/ml), and rHu steel factor (50 ng/ml) for colony forming unit granulocyte/macrophage (CFU-GM), colony forming unit granulocyte/erythrocyte/macrophage/megakaryocyte (CFU-GEMM) or burst forming unit-erythrocyte (BFU-E) analysis. These assays respectively allow quantitation of effects on early subsets of granulocyte-macrophage, multipotential, and erythroid progenitor cells. Various concentrations of partially purified MC148R protein (as described in the Results section) were compared to purified MIP-1α (Collaborative Biomedical Products, Bedfor, Mass.). Cultures were incubated at 37° C. in 5% $CO_2$ and low (5%) oxygen tension for 14 days, and then scored using an inverted microscope. Three plates were scored per data point per study and expressed as a percent of control for that study.

EXAMPLE 2

Amplification and Cloning of the MC148R Region from MCV Types 1 and 2

Based on the published sequence of MCV 1 DNA, primers flanking the MC148R region were designed and used with either MCV 1 or MCV 2 DNA that had been extracted from clinical specimens. The same primer pair was used for both MCV 1 and MCV 2. The resulting DNA fragment produced by PCR™ synthesis was ~400 base pairs in size for both types. This fragment was then cloned into the PCR™ 3.1 vector and amplified in One Shot cells (Invitrogen, San Diego, Calif.). As shown in FIG. 1, sequencing of these cloned PCR™ products showed that the MCV 1 sequence was identical to the previously published sequence (Senkevich et al., 1996). The MCV 2 sequence had 89% homology to the type 1 sequence. Amino acid comparisons showed 87% homology of the complete sequences, and 86% when the putative leader sequence was removed. The four conserved cysteine residues characteristic of C—C chemokines appear to be conserved in both of the MCV 1 and MCV 2 proteins. Based on sequence comparisons with macrophage chemoattractant protein-1 (MCP-1), the first 24 amino acids compose a leader sequence and the next five amino acids constitute the active site. This contrasts to MCP-1 which has 10 amino acids at the amino-terminal active site. MCV 1 and MCV 2 have very similar amino acid composition at the putative active site, except for a serine in MCV 2 instead of an alanine at position 26. Both proposed signal peptides share conserved regions near the putative cleavage sites.

EXAMPLE 3

Expression and Purification of the MC148R Proteins

The PCR™ products containing the MC148R regions from each MCV type were excised from PCR™ 3.1 and subcloned into the baculovirus expression vector, pVL1392. Sf9 insect cells were co-transfected with the pVL-MC1 or pVL-MC2 plasmid and baculovirus DNA containing a lethal deletion to make recombinant baculovirus. Sf9 cells infected with recombinant virus were then grown in protein-free medium. Because all known chemokines bind strongly to heparin, the clarified medium was then passed over a heparin-sepharose column and eluted with a KCl salt gradient. The fraction that contained a discernible band of 9 kDa (the predicted molecular weight of the mature protein) on SDS-PAGE was then partially purified by removing high molecular weight contaminants. After partial purification, each preparation consisted of a prominent 9 kDa band on a Coomassie-stained gel. The only other band that was visible was a faint band at ~6 kDa. The protein concentration was measured and the partially purified preparations of the two viral chemokines were used in functional assays. Medium from cells that had been transfected with the pVL 1392 vector alone was similarly processed and showed no band in the 9 kDa size range. The preparation from cells transfected with vector alone was used as a control for the functional assays.

EXAMPLE 4

Chemotactic Activity of MC148R1 and MC148R2 Proteins

Figure 2B:
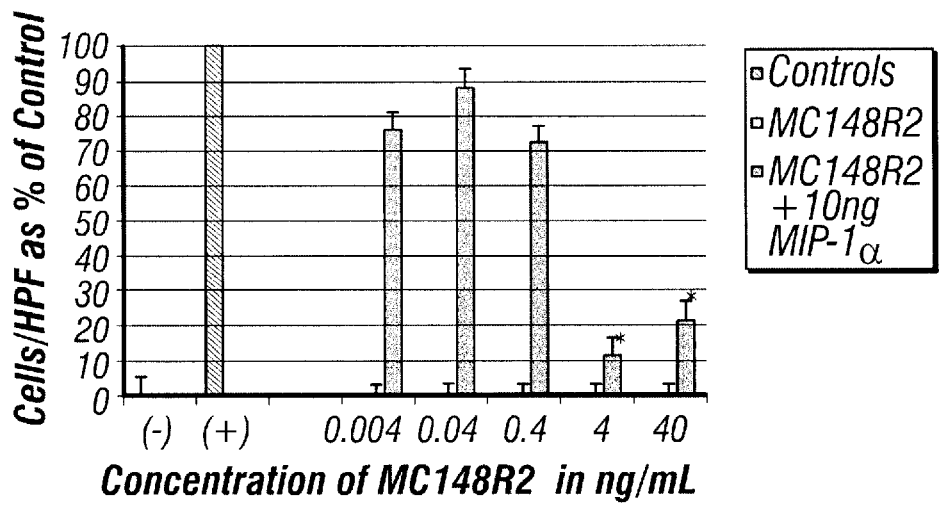
Figure 2C:
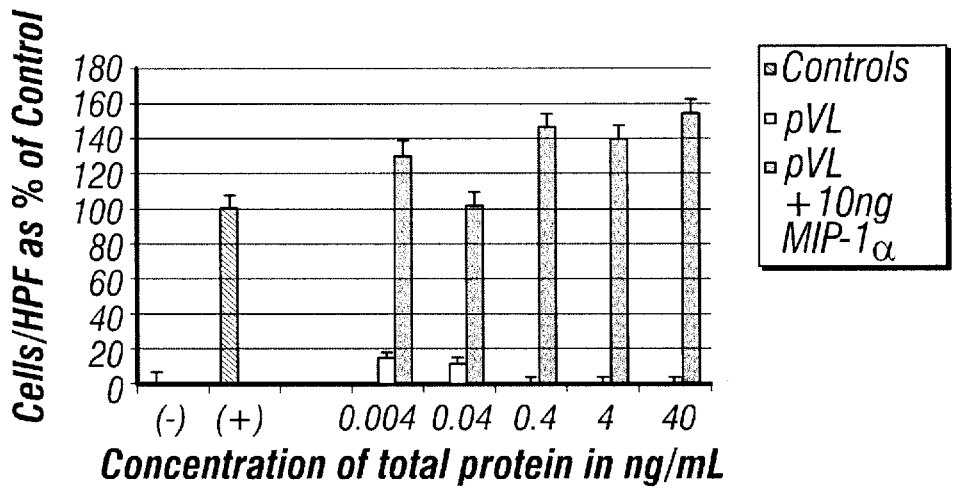
Figure 3A:
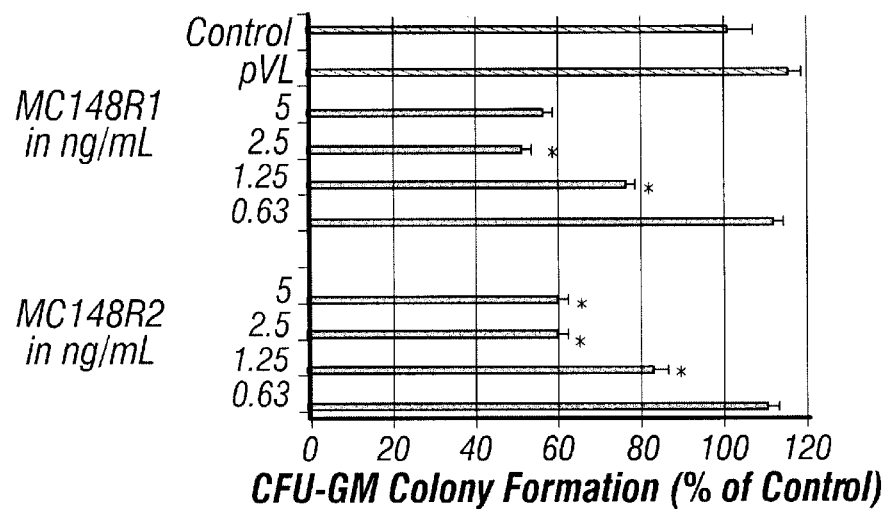
FIG. 3A, FIG. 3B and FIG. 3C. Effects of the viral chemokine-like proteins on the proliferation of hematopoietic progenitor cells.
Figure 3B:
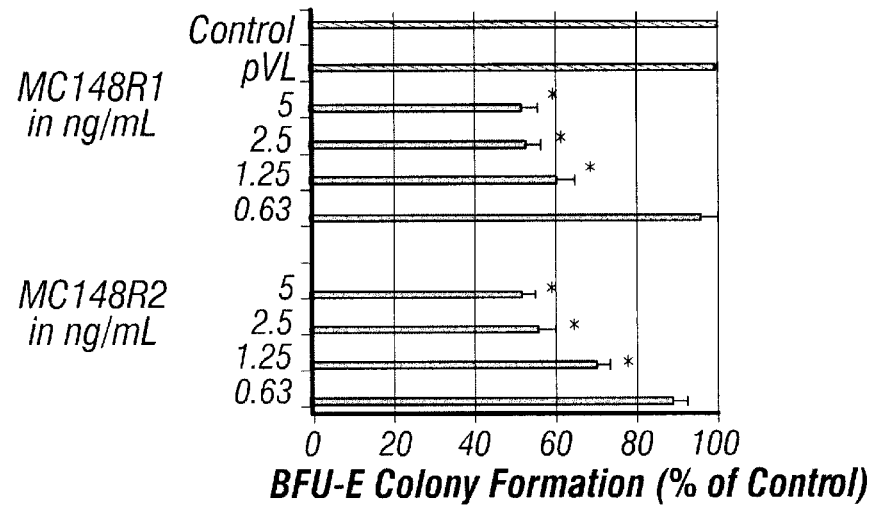
Figure 3C:
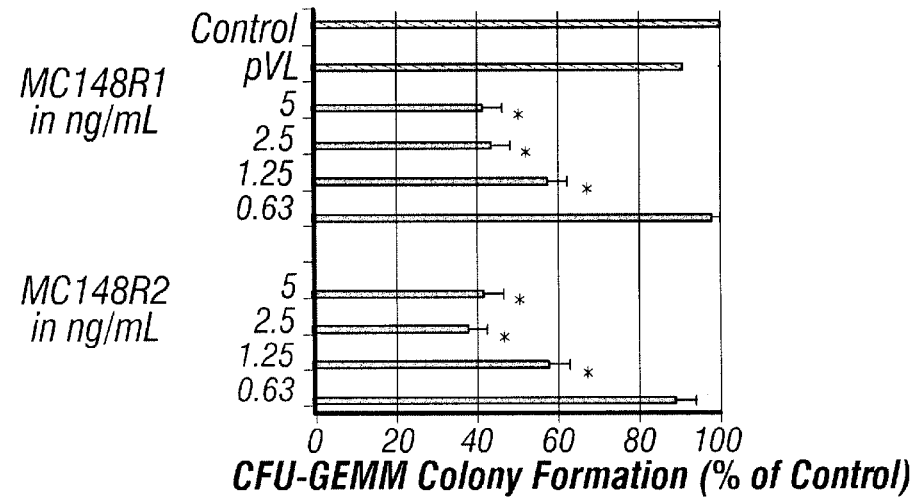

Since all chemokines are chemotactic by definition, the next series of studies were designed to test whether the synthesized proteins were chemotactic for monocytes. The partially purified MC148R1 and MC148R2 proteins were assayed for chemotactic activity by placing the test protein in medium which was separated from human peripheral blood mononuclear cells by a membrane. The number of cells migrating through the membrane in response to the protein were counted and expressed as a percentage of controls. As shown in FIG. 2, neither viral protein had significant chemotactic activity over a 10,000 fold concentration range compared to MIP-1α, the positive control. However, when either viral protein was present in the same well as MIP-1α, there was a marked inhibition of the expected chemotactic response. This effect was dependent on the concentration of the viral protein present. At very low concentrations of the viral protein, the number of migrating cell was statistically no different from the number migrating to MIP-1α alone. At higher concentrations of the viral protein, the number of migrating cells became no different than the number of cells migrating to the negative control. The recombinant viral proteins had no effect on cell viability. All experimental and control wells had 95–97% cell viability (measured by trypan blue exclusion) after incubation under assay conditions. The protein preparation from cells transfected with vector alone gave no chemotactic response and did not show any ability to block the chemotactic response of MIP-1α.

EXAMPLE 5

Effect of MC148R1 and MC148R2 on Hematopoietic Progenitor Cell Growth

Chemokines have been shown to inhibit colony formation of hematopoietic progenitor cells (Broxmeyer et al., 1995; Broxmeyer et al., 1993; Broxmeyer et al., 1990). To determine if the viral proteins shared this property, mononuclear cell fractions of bone marrow cells obtained from normal human donors were cultured in the presence of erythropoietin, interleukin-3, and steel factor (early acting cytokines that allow detection of early, more immature subsets of myeloid progenitor cells (Broxmeyer et al., 1995; Broxmeyer et al., 1993; Broxmeyer et al., 1990) in the presence or absence of the viral chemokine-like proteins. Both viral proteins inhibited colony formation of myeloid, erythroid, and multipotential progenitor cells by nearly 50% at concentrations as low as 1.25 to 2.5 ng/mL (FIG. 2). The plateau concentrations of MIP-1α that inhibit colony formation are 50–100 ng/mL, with less inhibition noted at 25 ng/mL and no inhibition at 1–10 ng/mL (Broxmeyer et al., 1995; Broxmeyer et al., 1993; Broxmeyer et al., 1990). Thus, the inhibitory concentrations of the viral proteins that show inhibition in this assay are lower than these concentrations of MIP-α. The degree of inhibition (between 40% and 60%) was equal to that seen in the same studies using 100 ng/mL of MIP-1α. Preparations from transfections using the pVL 1392 vector alone had no effect on cell growth or differentiation in this assay.

EXAMPLE 6

Production of Bacterially-Expressed MC148R Protein

The present example provide an alternative to the baculovirus system for producing the MC148R protein. The inventors chose the most likely cleavage site (based on analogy with other chemokines), amplified the corresponding DNA sequence from the clone of the full-length open reading frame of the MCV type 1 protein, and cloned it into the vector pCAL-n-EK (Stratagene, La Jolla, Calif.). This vector produces a fusion protein between the target gene and the calmodulin binding protein with an enterokinase cleavage site at the exact amino terminus of the target protein. After expression of the fusion protein, the fusion can be readily purified by passage over a calmodulin column and then cleaved with enterokinase to release the MC148R protein.

Analysis of the bacterially-expressed MC148R protein in the chemotaxis assay showed comparable inhibition of mononuclear cell migration in response to MIP-1α as that from the baculovirus system. The effect of the bacterially-expressed protein on bone marrow progenitor cells was not measured, but other chemokines expressed in bacterial systems or chemically synthesized are fully functional (Hromas et al., 1997a; Hromas et al., 1997b). The inventors conclude that the bacterially-expressed MC148R protein is functionally equivalent to the baculovirus-produced product. This bacterial expression system will permit production of milligram quantities of the MC148R protein.

EXAMPLE 7

Production of a Polyclonal Antibody to MC148R

In order to detect the MC148R protein in tissue and to develop a reagent for performing additional studies, the inventors prepared a polyclonal antibody to the MC148R protein. The baculovirus-expressed MC148R from MCV type 1 was run on a polyacrylamide gel and the 8 kDa band cut out and eluted. The protein was mixed with complete Freund's adjuvant and used to immunize a New Zealand white rabbit. Booster doses in incomplete Freund's adjuvant were administered at 2 and 4 wk and a terminal bleed was performed at 6 wk. A 4 wk test bleed serum was used in a western blot assay, using the bacterially-expressed MC148R protein as antigen.

The purified and cleaved bacterially-expressed MC148R protein was run on a 15% SDS polyacrylamide gel and electrophoretically transferred to nitrocellulose. After blocking, preimmune or various dilutions of immune rabbit serum was added to sections of the membrane and incubated overnight. The membrane was washed and peroxidase-conjugated goat anti-rabbit antibody was added, followed by additional washing and incubation with a peroxidase substrate (NBT/BCIP). The pre-immune serum showed no reaction. A 1:1000 dilution of immune serum demonstrated a strong reaction with the 8 kDa MC148R protein. Given the methods an compositions of the present invention, additional polyclonal and/or monoclonal antibodies may be generated.

EXAMPLE 8

Characterization of MC148R Receptor Binding

The inventors have shown that MC148R protein blocks the chemotactic activity of chemokines. It may be that the MCV chemokine-like protein blocks chemotaxis by either binding (but not activating) chemokine receptors or by forming inactive complexes with natural chemokines. The present Example outlines procedures that will elucidate the MC148R receptor interactions.

In order to examine the receptor interactions, cell lines that are transfected with cloned chemokine receptors and stably express the receptors are used. Initially the binding and activation of the receptors CCR 1, CCR 2, CCR 3, CCR 4, CCR 5, CCR 6, and CXCR 4 may be examined. Because MC148R blocks chemotaxis to MIP-1α, it is logical to examine CCR 1, CCR 4, and CCR 5, the receptors to which MIP-1α is known to bind. Because MC148R resembles a C—C chemokine, it also is logical to examine the other two C—C chemokine receptors. The HHV 8 vMIP II protein has been shown to bind to CXCR 4 (Kledal et al., 1997), so this is another logical receptor to examine. The inventors will also study the recently described CCR 6 (Baba et al., 1997; Greaves et al., 1997). CCR 6 is expressed in Langerhans cells, a possible target of MC148R. Given the known sequence of CCR 6 it may be cloned from Langerhans cells by reverse transcriptase PCR™ and expressed in 293 cells.

The above investigation generally will employ a competitive binding assay in which various concentrations of bacterially-expressed MC148R are added to a well containing a fixed amount of $^{125}$I-labeled chemokine and $2\times10^5$ receptor-expressing cells in binding buffer (50 mM HEPES, 1 mM CaCl$_2$, 5 mM MgCl$_2$, 0.5% BSA) are further added. After incubation at room temperature, the cell suspension is filtered through a Whatman GFC filter, washed, and counted. Controls include a homologous unlabeled chemokine competitor to define 100% competition. The chemokines to be labeled for use will be MIP-1α for CCR 1, CCR 4, and CCR 5, MCP-1 for CCR 2, RANTES for CCR 3, Exodus-1 (MIP-3α) for CCR 6, and SDF-1 for CXCR 4. All but SDF-1 and Exodus-1 are currently available in labeled form from Amersham.

Labeled SDF-1 or Exodus-1 may be made using $^{125}$I-Bolton-Hunter reagent. The competitive binding assay does not definitively prove that MC148R binds receptors—only that it prevents the binding of natural ligands. To more directly demonstrate receptor binding, the MC148R protein may be labeled using $^{125}$I-Bolton-Hunter reagent and the labeled protein may be added to receptor-expressing cells as above. The specificity of binding may be tested by competition with various concentrations of unlabeled MC148R protein or with an irrelevant protein (such as BSA). If receptor binding of MC148R is demonstrated using the labeled viral protein, then the reciprocal competition studies is performed with unlabeled human chemokines to confirm the results initially generated.

Upon identification of receptor binding, the receptors to which binding is demonstrated can be evaluated for activation. To evaluate activation of the receptors, calcium flux assays can be performed using a calcium-binding chromophore that shifts its fluorescence emission wavelength upon binding free calcium which has been released into the cytosol (Grynkiewicz et al., 1985). In such an assay receptor-expressing cells are loaded with Fura-2 by incubation in Hank's buffered saline with calcium and magnesium, 10 mM HEPES, and 2.5 μM Fura-2 in the dark at 37° C. After washing, the cells are placed in a fluorimeter cuvette (with stirring) and various quantities of MC148R or control chemokines are added. The ratio of fluorescence at 340 nM (the peak wavelength in the absence of free calcium) and 380 nM (the peak wavelength in the presence of free cytosolic calcium) are monitored over time for evidence of calcium mobilization. Typically, these wavelength shifts appear within a few seconds of adding the receptor ligand. If evidence of calcium mobilization is found, the reactions can be repeated in calcium-free medium in the presence of EDTA to confirm that intracellular calcium is mobilized.

EXAMPLE 9

Determine the Regions of the MC148R Protein that are Functionally Important for Inhibition of Chemotaxis As MC148R is a natural inhibitor of chemokines, a mutagenesis study of MC148R should expand the understanding of both normal and abnormal chemokine function. Modifying regions of the MC148R protein will provide such an understanding. Two regions lend themselves to these types of studies. The first is the amino terminus, a region known to be involved in receptor binding. The other region to be modified is the proteoglycan binding site which has been reported to be important for chemotactic activity (Graham et al., 1996).

In general, the mutagenesis strategies may use PCR™-based methods to generate MC148R molecules with altered sequences. The first set of mutants will be ones in which the amino terminal deletion is "restored". PCR™ primers located at the 5' end of the sequence encoding the mature protein (ie. the protein after cleavage of the signal peptide) will be made with 5' extensions of 3, 6, 9, 12, or 15 nucleotides thus adding 1, 2, 3, 4, or 5 amino acids to the amino terminus of the protein. The sequence added may be that of MCP-1 (QPDAI (SEQ ID NO:10)) as this chemokine has the most homology elsewhere in the mature protein. These primers are illustrated in the Table 4 below:

TABLE 4

Primers for Amino Terminal Mutagenesis

| DNA Sequence | | Amino Acid Sequence | |
|---|---|---|---|
| CTCGCGAGACGGAAATGTTGT | (SEQ ID NO:11) | LARRKCC | (SEQ ID NO:12) |
| ATCCTCGCGAGACGGAAATGTTGT | (SEQ ID NO:13) | ILARRKCC | (SEQ ID NO:14) |
| GCGATCCTCGCGAGACGGAAATGTTGT | (SEQ ID NO:15) | AILARRKCC | (SEQ ID NO:16) |
| GACGCGATCCTCGCGAGACGGAAATGTTGT | (SEQ ID NO:17) | DAILARRKCC | (SEQ ID NO:18) |
| CCCGACGCGATCCTCGCGAGACGGAAATGTTGT | (SEQ ID NO:19) | PDAILARRKCC | (SEQ ID NO:20) |
| CAACCCGACGCGATCCTCGCGAGACGGAAATGTTGT | (SEQ ID NO:21) | QPDAILARRKCC | (SEQ ID NO:22) |

Cloned MC148R DNA can be amplified using one of the above primers for the 5' primer each using the same 3' primer located at the end of the coding sequence. Note that the actual primers used have additional sequences at the 5' end which are required by the cloning vector to allow high efficiency, ligation-independent cloning. The PCR™ product can be cloned into the pCAL-n-EK (Stratagene) vector and sequenced to confirm the predicted sequence. Once the sequence is confirmed, a large volume culture can be grown and induced to produce calmodulin binding protein-MC148R fusion protein. The fusion protein then can be purified on a calmodulin column and the chemokine released by enterokinase cleavage.

The mutant proteins thus generated then are assayed for chemotactic activity and for the ability to block chemotaxis to MIP-1α using the Boyden chamber assay. If chemotaxis is restored in some of the mutants, the added amino acids will be modified (by using a different primer sequence and repeating the steps outlined above) to further characterize the effect. Modifications will be based on the sequence of other chemokines in that region or by substituting a "generic" amino acid such as alanine for critical residues.

To mutate the proteoglycan binding region, overlap PCR™ mutagenesis can be used. The critical sequence identified in MIP 1-α as the proteoglycan binding region is K-R-S-R (SEQ ID NO:23). Mutation of two of the lysine or arginine residues eliminates heparin binding and also abolishes chemotactic activity. The corresponding sequence in MC148R (for both type 1 and type 2) is Q-D-G-R (SEQ ID NO:24). Although this protein binds heparin, it does so much more weakly than do most human chemokines (Krathwohl et al., 1997). Thus, the proteoglycan binding region may be "restored" by mutating the Q-D-G-R (SEQ ID NO:24) to K-R-S-R (SEQ ID NO:23). Primers from both strands which include the region to be mutated and several codons on either side will be made with the mutant sequence. In this case, the examples of wild type and mutant sequences to be used are shown in the Table 5 below:

TABLE 5

Primers for Proteoglycan Binding Region Mutagenesis

| DNA Sequence | | Protein Sequence | |
|---|---|---|---|
| GTGACGCTGCAAGACGGAAGACAAGGCTGC | SEQ ID NO:25 | VTLQDGRQGC (wild type) | SEQ ID NO:26 |
| GCAGCCTTGTCTTCCGTCTTGCAGCGTCAC | SEQ ID NO:27 | Complement (wild type) | |
| GTGACGCTGAAAAGGTCAAGACAAGGCTGC | SEQ ID NO:28 | VTLKRSRQGC (mutant) | SEQ ID NO:29 |
| GCAGCCTTGTCTTGACCTTTTCAGCGTCAC | SEQ ID NO:30 | Complement | |

The mutant oligonucleotide (sense strand) is paired with a downstream primer from the end of the MC148R region for a PCR™ reaction while the antisense mutant oligonucleotide is paired with an upstream primer located at the beginning of the MC148R region for a separate PCR™ reaction. The two PCR™ products can be gel purified and combined with the PCR™ primers located at the beginning and end of the MC148R region for another PCR™ reaction. The primers in the latter reaction contain the extensions to allow cloning into the pCAL-n-EK vector (Stratagene) at the end of this reaction. The insert can be sequenced to confirm that the correct (i.e. mutated) sequence is present and the protein will be expressed and purified as above. The recombinant protein will then be tested for chemotactic and chemotaxis inhibition activity. Given the way the amino terminal variants noted above are generated, it will be well within the skill of one in the art to make various combinations of mutations in the two areas of the molecule. Depending on the results of the proteoglycan region mutants, additional mutations may also be generated.

Alternatively, it is possible that MC148R protein will neither bind nor activate any chemokine receptors. If this is the case, additional studies to determine the mechanism of inhibition of chemotaxis by MIP-1α (and possibly other chemokines) may be performed. One possibility that will be examined is that MC148R forms complexes with human chemokines and prevents binding to receptors. This possibility will be examined by mixing MC148R protein with MIP-1α (or other chemokines) at various concentrations and immunoprecipitating the MC148R using the polyclonal rabbit antiserum and examining the immune complex for human chemokine. The converse experiment (immunoprecipitation using the appropriate anti-chemokine antibody) can also be done. If complexes cannot be demonstrated, the inventors will perform competition assays for receptor activation. For example, CCR5 expressing cells will be loaded with Fura-2 and exposed to MIP-1α in the presence of varying concentrations of MC148R. If MIP-1α were able to activate CCR5 normally in the presence of MC148R, this would suggest that the inhibition of chemotaxis is mediated by a mechanism other than blocking the receptor or complexing with the chemokine.

EXAMPLE 10

The Effect of MC148R on Cultured Langerhans Cells

Given that MC148R inhibits bone marrow progenitor colony formation, it is likely that the MCV chemokine-like protein inhibits the growth and/or differentiation of Langerhans cells because both the bone marrow progenitors and Langerhans cells are derived from low-density $CD34^+$ bone marrow cells. As an absence of Langerhans cells has been noted in clinical MCV lesions, it is likely that a viral gene product is responsible and MC148R appears to be a good candidate. As Langerhans cells normally migrate to the skin from the blood, mature, acquire foreign antigens, and subsequently exit the skin and migrate to regional lymph nodes, there are several points at which MC148R could act. The present example is directed toward the determination of the effect of MC148R on Langerhans cells.

Effect of MC148R on the growth and differentiation of Langerhans cells. To conduct these studies, the inventors will first establish cultures of human Langerhans cells. There are two potential sources of Langerhans cells, bone marrow (or cord blood) (Caux et al., 1992) and peripheral blood (Bender et al., 1996). While both systems yield cells with surface markers of Langerhans cells (and eventually dendritic cells), it is not clear if both systems produce cells that are equivalent. A number of studies have suggested that there are important differences in the cells produced by the two approaches, even though the dendritic cells that are eventually produced have the same surface markers and ability to present antigen.

Most studies suggest that the marrow-derived dendritic cells are most like Langerhans cells. Therefore, the inventors will generate Langerhans cells from bone marrow progenitor cells, but it is understood that the alternate system may also be used. For the bone marrow system, CD34$^+$ cells are purified from normal human bone marrow by immune "panning" and immunomagnetic bead selection. This procedure yields cell populations that are >95% CD34$^+$. The cells are then grown in RPMI 1640 with 10% fetal bovine serum supplemented with GM-CSF (200 U/ml) and TNFα (50 U/ml) at an initial cell density of $10^5$ per ml. Cells can be monitored microscopically for formation of cells with dendritic processes.

Assays are performed at a standard time after initiation, probably between 12 and 15 days. The optimal time can be determined by preliminary studies in which cells are withdrawn from culture at 2 day intervals beginning at day 7 and assayed for expression of CD1a, CD80, CD83, and CD86 by monoclonal antibody staining followed by flow cytometry. The CD1a marker is a general marker for dendritic-type cells while the others are differentiation/maturation markers. The time that reproducibly yields 50–60% CD1a$^+$ cells will be selected as the assay time.

Several sets of studies will be conducted to examine several potential effects of the viral protein on Langerhans cells. These potential effects are not mutually exclusive, so any or all, of these studies may be conducted. In addition, parallel studies with several human chemokines may be conducted. As some chemokines are known to inhibit hematopoiesis while others have no effect, it is likely that only a subset of chemokines will have an effect on Langerhans cells. The human chemokines to be studied will include MIP-1α, MCP-1, Exodus 1 (MIP-3α), (all chemokines that inhibit hematopoiesis) and RANTES and eotaxin (chemokines that do not inhibit hematopoiesis). The first set will examine the effect of MC148R or human chemokines on the growth of Langerhans cells. Several concentrations of MC148R or chemokine protein will be added to the medium at several different times prior to assay. For example, if 14 days in culture is the assay time, test protein is added at 3, 6, 9, and 12 days and the total number of viable cells and the percent CD1a, CD80, or CD86 positive determined at day 14. Depending on the results, additional studies examining limited exposure to the test protein (e.g., days 3–6) and competition studies between MC148R and active chemokines may also be conducted.

It is possible that the viral protein blocks chemokine-mediated migration of Langerhans cells into the epithelium in much the same way that it blocks migration of peripheral blood mononuclear cells. Dendritic cells have been shown to migrate in response to some, but not all chemokines (Sozzani et al., 1997). However, the paper that reported this effect used dendritic cells cultured from peripheral blood so the panel of human chemokines also may be tested on the marrow-derived dendritic cells in a Boyden chamber assay as described in (Krathwohl et al., 1997) and in preliminary studies to determine if the same chemokines are active. Once the active chemokines are identified, competition studies between MC148R and chemokines similar to those described above and in reference (Krathwohl et al., 1997) may be performed.

Another possible effect of MC148R on Langerhans cells is to trigger them to migrate from the epithelium (with or without antigen). To examine this possibility, the two markers associated with migrating Langerhans cells, several CD44 isoforms (CD44v5, CD44v6, CD44v9) (Weiss et al., 1997) and α6 integrin (Price et al., 1997) may be monitored by e.g., flow cytometry. Preliminary studies to determine the normal expression CD44 isoforms and α$_6$ integrin in the cultured cells may be useful. The initial study that reported expression of CD44 isoforms in migrating Langerhans cells examined these markers in cultured cells derived from skin ("true" Langerhans cells) and those derived from blood. As noted above, the marrow-derived cells may more accurately reflect behavior of cells derived from skin. As above, parallel studies with human chemokines also may be conducted. Of particular interest are the effects of Exodus 1 (MIP-3α) as it is the only known chemokine that binds to CCR 6, a receptor highly expressed on dendritic cells.

Investigation of region(s) of MC148R responsible for effects on Langerhans cells. Upon demonstration of an MC148R-mediated effect on Langerhans cells, the present invention further contemplates identification of the location of the regions of the chemokines that interact with Langerhans cells. Such investigations may use mutants of the MC148R protein generated as described above. Growth, maturation, migration, and/or migration marker expression studies will be conducted as outlined above using the mutant viral chemokine proteins. Both the amino terminal and proteoglycan binding region mutants will be studied.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alkhatib et al., "CC CKR5: a RANTES, MIP-1alpha, MIP-1beta receptor as a fusion cofactor for macrophage-tropic HIV-1," *Science*, 272(5270):1955–1958, 1996.

Arya et al., "Human immunodeficiency virus type 2 lentivirus vectors for gene transfer: expression and potential for helper virus-free packaging," *Hum Gene Ther.*, 9(9):1371–1380, 1998.

Athauda, et al., *J. Biochem.*, 113:742–746, 1993.

Baba, et al., "Identification of CCR6, the specific receptor for a novel lymphocyte-directed CC chemokine LARC," *J. Biol. Chem.*, 272:14893–14898, 1997.

Baggiolini, et al., "Interleukin-8 and related chemotactic cytokines—CXC and CC chemokines" *Adv. Immunol.*, 55:97–179, 1994.

Baichwal and Sugden, "Vectors for gene transfer derived from animal DNA viruses: Transient and stable expression of transferred genes", *Gene Transfer*, Kucherlapati (Ed), New York, Plenum Press, pp. 117–148, 1986.

Barany and Merrifield, "The Peptides," Gross and Meienhofer (Eds), Academic Press, New York, pp. 1–284, 1979.

Bender et al., "Improved methods for the generation of dendritic cells from nonproliferating progenitors in human blood," *J. Immunol. Meth.*, 196:121–135, 1996.

Benvenisty & Neshif, "Direction introduction of genes into rats and expression of the genes," *Proc. Nat. Acad Sci. USA*, 83:9551–9555, 1986.

Birthistle and Carrington, "Molluscum Contagiosum Virus" *J. Infect.*, 34:21–28, 1997.

Blomer et al., "Highly efficient and sustained gene transfer in adult neurons with a lentivirus vector," *J. Virol.*, 71(9):6641–6649, 1997.

Bolton and Hunter, *J. Biochem.*, 133:529, 1973.

Boyden, "The chemotactic effect of mixtures of antibody and antigen on polymorphonuclear leukocytes" *J. Exper. Med.*, 115:453–460, 1962.

Braxton and Wells, *Biochemistry*, 31:7796–7801, 1992.

Broxmeyer, et al., "Comparative analysis of the human macrophage inflammatory protein family of cytokines (chemokines) on proliferation of human myeloid progenitor cells," *J. Immunol.*, 150:3448–3458, 1993.

Broxmeyer, et al., "Enhancing and suppressing effects of recombinant murine macrophage inflammatory proteins on colony formation in vitro by bone marrow myeloid progenitor cells," *Blood*, 76:1110–1116, 1990.

Broxmeyer, et al., "Human chemokines: enhancement of specific activity and effects in vitro on normal and leukemic progenitors and a factor-dependent cell line and in vivo in mice," *Ann. Hematol.*, 71:235–246, 1995.

Buller, et al., "Replication of molluscum contagiosum virus", *Virology*, 213:655–659, 1995.

Capaldi et al., *Biochem. Biophys. Res. Comm.*, 76:425, 1977.

Carter and Flotte, "Development of adeno-associated virus vectors for gene therapy of cystic fibrosis," *Curr. Top. Microbiol. Immunol.*, 218:119–144, 1996.

Caux et al., "GM-CSF and TNF-α cooperate in the generation of dendritic Langerhans cells," *Nature*, 360:258–261, 1992.

Cech et al., *Cell*, 27:487–496, 1981.

Chang et al., "Foreign gene delivery and expression in hepatocytes using a hepatitis B virus vector", *Hepatology*, 14:124A, 1991.

Chatterjee, et al., "Strategies for efficient gene transfer into hematopoietic cells: The use of adeno-associated virus vectors in gene therapy," *Ann. N.Y. Acad. Sci.*, 770:79–90, 1995.

Chen and Okayama, "High-efficiency transfection of mammalian cells by plasmid DNA," *Mol. Cell Biol.*, 7:2745–2752, 1987.

Choe et al., "The beta-chemokine receptors CCR3 and CCR5 facilitate infection by primary HIV-1 isolates," *Cell*, 85(7):1135–1148, 1996.

Clark-Lewis, et al., "Structure-activity relationships of chemokines", *J. Leukocyte Biol.*, 57:703–711, 1995.

Cocchi, et al., "Identification of RANTES, MIP-1 α, and MIP-1 β, as the major HIV-suppressive factors produced by CD8+ T cells", *Science*, 270:1811–1815, 1995.

Coffin, "Retroviridae and their replication," In: *Virology*, Fields and Knipe (Eds), New York Raven Press, pp. 1437–1500, 1990.

Couch et al., "Immunization with types 4 and 7 adenovirus by selective infection of the intestinal tract," *Am. Rev. Resp. Dis.*, 88:394–403, 1963.

Coupar et al., "A general method for the construction of recombinant vaccinia virus expressing multiple foreign genes," *Gene*, 68:1–10, 1988.

Darai et al., "Analysis of the genome of molluscum contagiosum virus by restriction endonuclease analysis and molecular cloning", *J. Med. Virol.*, 18:29–39, 1986.

Deng et al., "Identification of a major co-receptor for primary isolates of HIV-1," *Nature*, 381(6584):661–666, 1996.

Doranz et al., "A dual-tropic primary HIV-1 isolate that uses fusin and the beta-chemokine receptors CKR-5, CKR-3, and CKR-2b as fusion cofactors," *Cell*, 85(7):1149–1158, 1996.

Dragic et al., "HIV-1 entry into CD4+ cells is mediated by the chemokine receptor CC—CKR-5," *Nature*, 381 (6584):667–673, 1996.

Dubensky et al., "Direct transfection of viral and plasmid DNA into the liver or spleen of mice," *Proc. Nat. Acad. Sci. USA*, 81:7529–7533, 1984.

Fechheimer et al., "Transfection of mammalian cells with plasmid DNA by scrape loading and sonication loading," *Proc. Natl. Acad. Sci. USA*, 84:8463–8467, 1987.

Fenner and Nakano, In: *Laboratory Diagnosis of Infectious Diseases*, Vol. 2, Viral Rickettsial and Chlamydial Disease, Lennette et al., (Eds.) Springer-Verlag, New York (publ.), p177–207, 1988.

Ferkol et al., "Regulation of the phosphoenol pyruvate carboxy kinase/human factor IX gene introduced into the livers of adult rats by receptor-mediated gene transfer," *J. FASEB*, 7:1081–1091, 1993.

Ferrari et al., "Second-strand synthesis is a rate-limiting step for efficient transduction by recombinant adeno-associated virus vectors," *J. Virol.*, 70:3227–3234, 1996.

Fife et al., "Growth of molluscum contagiosum virus in a human foreskin xenograft model", *Virology*, 226:95–101, 1996.

Fisher et al., "Transduction with recombinant adeno-associated virus for gene therapy is limited by leading-strand synthesis," *J. Virol.*, 70:520–532, 1996.

Flotte et al., "Stable in vivo expression of the cystic fibrosis transmembrane conductance regulator with an adeno-associated virus vector," *Proc. Natl. Acad. Sci. USA*, 90:10613–10617, 1993.

Forster and Symons, "Self-cleavage of plus and minus RNAs of a virusoid and a structural model for the active sites," *Cell*, 49:211–220, 1987.

Fraley et al., "Entrapment of a bacterial plasmid in phospholipid vesicles: Potential for gene transfer," *Proc. Natl. Acad. Sci. USA*, 76:3348–3352, 1979.

Freshner, "Animal Cell Culture: a Practical Approach", Second Ed, Oxford, N.Y., IRL Press, Oxford University Press, 1992.

Friedmann, "Progress toward human gene therapy," *Science*, 244:1275–1281, 1989.

Gefter et al., *Somatic Cell Genet.*, 3:231–236, 1977.

Gerlach et al., "Construction of a plant disease resistance gene from the satellite RNA of tobacco rinspot virus," *Nature (London)*, 328:802–805, 1987.

Ghosh-Choudhury et al., *EMBO J.*, 6:1733–1739, 1987.

Ghosh and Bachhawat, "Targeting of liposomes to hepatocytes," In: *Liver diseases, targeted diagnosis and therapy using specific receptors and ligands*, Wu and Wu (Eds), New York, Marcel Dekker, pp. 87–104, 1991.

Goding, In: *Monoclonal Antibodies: Principles and Practice*, 2d ed., Academic Press, Orlando, Fla., pp. 60–61, and 71–74, 1986.

Gomez-Foix et al., *J. Biol. Chem.*, 267:25129–25134, 1992.

Gompels, et al., "The DNA sequence of human herpesvirus-6: structure, coding content, and genome evolution," *Virology*, 209:29–51, 1995.

Goodman, et al., "Recombinant adeno-associated virus-mediated gene transfer into hematopoietic progenitor cells," *Blood*, 84:1492–1500, 1994.

Gopal, "Gene transfer method for transient gene expression, stable transfection, and cotransfection of suspension cell cultures," *Mol. Cell Biol.*, 5:1188–1190, 1985.

Gossen and Bujard, *Proc. Natl. Acad. Sci. USA*, 89:5547–5551, 1992.

Gossen et al., *Science*, 268:1766–1769, 1995.

Gottlieb and Myskowski, "Molluscum contagiosum," *Int. J. Dermatol.*, 33:453–461, 1994.

Graham and Prevec, "Adenovirus-based expression vectors and recombinant vaccines," *Biotechnology*, 20:363–390, 1992.

Graham and Van Der Eb, "A new technique for the assay of infectivity of human adenovirus 5 DNA," *Virology*, 52:456–467, 1973.

Graham et al., "Characteristics of a human cell line transformed by DNA from human adenovirus type 5," *J. Gen. Virol.*, 36:59–72,1977.

Graham et al., "Identification and characterization of an inhibitor of haemopoietic stem cell proliferation," *Nature*, 344:442–444, 1990.

Graham et al., "Uncoupling of stem cell inhibition from monocyte chemoattraction in MIP-1 alpha by mutagenesis of the proteoglycan binding site", *EMBO J.*, 15:6506–6515, 1996.

Grandaliano et al., "Monocyte chemotactic peptide-1 expression and monocyte infiltration in acute renal transplant rejection," *Transplantation*, 63(3):414–420, 1997.

Greaves et al., "CCR6, a CC chemokine receptor that interacts with macrophage inflammatory protein 3 α and is highly expressed in human dendritic cells," *J. Exp. Med.*, 186:837–844, 1997.

Grunhaus and Horwitz, "Adenovirus as cloning vector," *Seminar in Virology*, 3:237–252, 1992.

Grynkiewicz et al., "A new generation of $Ca^{2+}$ indicators with greatly improved fluorescence properties," *J. Biol. Chem.*, 260:3440–3450, 1985.

Harland and Weintraub, "Translation of mammalian mRNA injected into Xenopus oocytes is specifically inhibited by antisense RNA," *J. Cell Biol.*, 101:1094–1099, 1985.

Harlow and Lane Antibodies: A Laboratory Manual, Cold Spring Harbor Laboratory, 1988.

Hebertetal, *J. Biol. Chem.*, 266:18989, 1991.

Hersdorffer et al., "Efficient gene transfer in live mice using a unique retroviral packaging line," *DNA Cell Biol.*, 9:713–723, 1990.

Herz and Gerard, "Adenovirus-mediated transfer of low density lipoprotein receptor gene acutely accelerates cholesterol clearance in normal mice," *Proc. Natl. Acad. Sci. USA*, 90:2812–2816, 1993.

Hodgson, *J. Bio/Technology*, 9:19–21, 1991.

Horwich et al., "Synthesis of hepadenovirus particles that contain replication-defective duck hepatitis B virus genomes in cultured HuH7 cells," *J. Virol.*, 64:642–650, 1990.

Hromas et al., "Cloning and characterization of exodus, a novel β-chemokine," *Blood*, 89:3315–3322, 1997a.

Hromas et al., "Isolation and characterization of Exodus-2, a novel C—C chemokine with a unique 37 amino acid carboxyl-terminal extension," *J. Immunol.*, 159:2554–2558, 1997b.

Johnson et al., "Peptide Turn Mimetics," In: *Biotechnology and Pharmacy*, Pezzuto et al., Eds., Chapman and Hall, New York 1993.

Jones and Shenk, "Isolation of deletion and substitution mutants of adenovirus type 5," *Cell*, 13:181–188, 1978.

Joyce, "RNA evolution and the origins of life," *Nature*, 338:217–244, 1989.

Kaneda et al., "Increased expression of DNA cointroduced with nuclear protein in adult rat liver," *Science*, 243:375–378,1989.

Kaplitt et al., *Nat. Genet.*, 8:148–153, 1994.

Kaplitt, et al., "Long-term gene transfer in porcine myocardium after coronary infusion of an adeno-associated virus vector," *Ann. Thor. Surg.*, 62:1669–1676, 1996.

Karlsson et al., *EMBO J.*, 5:2377–2385, 1986.

Kato et al., "Expression of hepatitis β virus surface antigen in adult rat liver," *J. Biol. Chem.*, 266:3361–3364, 1991.

Keller et al., "Re-assessment of Boyden's Technique For Measuring Chemotaxis", *J. Immunol. Meth.*, 165–168, 1972.

Kessler et al., "Gene delivery to skeletal muscle results in sustained expression and systemic delivery of a therapeutic protein," *Proc. Natl. Acad. Sci. USA*, 93:14082–14087, 1996.

Kim and Cech, "Three dimensional model of the active site of the self-splicing rRNA precursor or Tetrahymena," *Proc. Natl. Acad. Sci. USA*, 84:8788–8792, 1987.

Kledal et al., "A broad-spectrum chemokine antagonist encoded by Kaposi's sarcoma-associated herpesvirus," *Science*, 277:1656–1659, 1997.

Klein et al., "High-velocity microprojectiles for delivering nucleic acids into living cells", *Nature*, 327:70–73,1987.

Koeberl et al., "Persistent expression of human clotting factor IX from mouse liver after intravenous injection of adeno-associated virus vectors," *Proc. Natl. Acad. Sci. USA*, 94:1426–1431, 1997.

Kohler and Milstein, *Eur. J. Immunol.* 6:511–519, 1976.

Kohler and Milstein, *Nature* 256:495–497,1975.

Krathwohl et al., "Functional characterization of the C—C chemokine-like molecules encoded by molluscum contagiosum virus types 1 and 2," *Proc. Natl. Acad. Sci. USA*, 94:9875–9880, 1997.

Kyte anf Doolittle, "A simple method for displaying the hydropathic character of a protein," *J. Mol.*

Le Gal La Salle et al., "An adenovirus vector for gene transfer into neurons and glia in the brain," *Science*, 259:988–990, 1993.

Levrero et al., "Defective and nondefective adenovirus vectors for expressing foreign genes in vitro and in vivo," *Gene*, 101:195–202, 1991.

MacDonald et al., "Late expression of a β chemokine homolog by murine cytomegalovirus" *J. Virol.*, 71:1671–1678, 1997.

Macejak and Sarnow, *Nature*, 353:90–94, 1991.

Mann et al., "Construction of a retrovirus packaging mutant and its use to produce helper-free defective retrovirus," *Cell*, 33:153–159, 1983.

Mantovani et al., "The chemokine superfamily: Crosstalk with the IL-1 system," *Immunobiol.*, 195:522–549, 1996.

Markowitz et al., "A safe packaging line for gene transfer: Separating viral genes on two different plasmids," *J. Virol.*, 62:1120–1124, 1988.

Martinet al., "Blood Monocyte Chemotaxis," *J. Immunol. Meth.*, 174:209–214, 1994.

McColl et al., *J. Immunol.*, 150:4550–455, 1993.

McCown et al., "Differential and persistent expression patterns of CNS gene transfer by an adeno-associated virus (AAV) vector," *Brain Res.*, 713:99–107, 1996.

Merrifield, *Science*, 232: 341–347, 1986

Michel and Westhof, "Modeling of the three-dimensional architecture of group I catalytic introns based on comparative sequence analysis," *J. Mol. Biol.*, 216:585–610, 1990.

Mizukami et al., "Adeno-associated virus type 2 binds to a 150-kilodalton cell membrane glycoprotein," *Virology*, 217:124–130, 1996.

Moore et al., "Molecular mimicry of human cytokine and cytokine response pathway genes by KSHV," *Science*, 274, 1739–1744, 1996.

Mulligan, "The basic science of gene therapy," *Science*, 260:926–932, 1993. Myers, EPO 0273085

Nicholas et. al., "Kaposi's sarcoma-associated human herpesvirus-8 encodes homologues of macrophage inflammatory protein-1 and interleukin-6," *Nat. Med.*, 3:287–292, 1997.

Nicolas and Rubenstein, "Retroviral vectors," In: *Vectors: A survey of molecular cloning vectors and their uses*, Rodriguez and Denhardt (Eds.), Stoneham Butterworth, pp. 493–513, 1988.

Nicolau and Sene, "Liposome-mediated DNA transfer in eukaryotic cells," *Biochem. Biophys. Acta*, 721:185–190, 1982.

Nicolau et al., "Liposomes as carriers for in vivo gene transfer and expression," *Methods Enzymol.*, 149:157–176, 1987.

Oberlin et al., "The CXC chemokine SDF-1 is the ligand for LESTR/fusin and prevents infection by T-cell-line-adapted HIV-1," *Nature*, 382:833–835, 1996.

Paskind et al., "Dependence of moloney murine leukemia virus production on cell growth," *Virology*, 67:242–248, 1975.

Pattison et al., "RANTES chemokine expression in cell-mediated transplant rejection of the kidney," *Lancet*, 343(8891):209–211, 1994.

Pattison et al., "RANTES chemokine expression in transplant-associated accelerated atherosclerosis," *J. Heart Lung Transplant*, 15(12)1194–1199, 1996.

Paul, *Fundamental Immunology*, 3rd Ed., Raven Press, New York City, pp 822–826 1993.

Pelletier and Sonenberg, *Nature*, 334:320–325, 1988.

Perales et al., "Gene transfer in vivo: Sustained expression and regulation of genes introduced into the liver by receptor-targeted uptake," *Proc. Natl. Acad. Sci. USA*, 91:4086–4090, 1994.

Pickup, "Poxviral modifiers of cytokine responses to infection," *Infectious Agents and Disease—Reviews Issues and Commentary*, 3:116–127, 1994.

Ping et al., "Altered β-adrenergic receptor signaling in heart failure, in vivo gene transfer via adeno and adeno-associated virus," *Microcirculation*, 3:225–228, 1996.

Porter et al., In: *Molecular and Cell Biology of Sexually Transmitted Diseases,.* Wright and Archard (Eds), Chapman and Hall Ltd. London (publ.), p 233–257, 1992

Porter et al., "Molluscum contagiosum virus types in genital and non-genital lesions," *Br. J. Dermatol.*, 120:37–41, 1989.

Potter et al., "Enhancer-dependent expression of human k immunoglobulin genes introduced into mouse pre-B lymphocytes by electroporation," *Proc. Nat. Acad. Sci. USA*, 81:7161–7165, 1984.

Price et al., "$\alpha_6$ integrins are required for Langerhans cell migration from the epidermis," *J. Exp. Med.*, 186:1725–1735, 1997.

Racher et al., *Biotechnology Techniques*, 9:169–174, 1995.

Ragot et al., "Efficient adenovirus-mediated transfer of a human minidystrophin gene to skeletal muscle of mdx mice," *Nature*, 361:647–650, 1993.

Ray and Gately III, "Dermatologic manifestations of HIV infection and AIDS" *Infect. Dis. Clinics North Am.*, 8:583–605, 1994.

Reinhold-Hurek and Shub, "Self-splicing introns in tRNA genes of widely divergent bacteria," *Nature*, 357:173–176, 1992.

Renan, "Cancer genes: Current status, future prospects and applications in radiotherapy/oncology," *Radiother. Oncol.*, 19:197–218, 1990.

Rich et al., "Development and analysis of recombinant adenoviruses for gene therapy of cystic fibrosis," *Hum. Gene Ther.*, 4:461–476, 1993.

Ridgeway, "Mammalian expression vectors," In: *Vectors: A survey of molecular cloning vectors and their uses*, Rodriguez and Denhardt (Eds), Stoneham Butterworth, pp. 467–492, 1988.

Rippe et al., "DNA-mediated gene transfer into adult rat hepatocytes in primary culture," *Mol. Cell Biol.*, 10:689–695, 1990.

Rosenfeld et al., "Adenovirus-mediated transfer of a recombinant α1-antitrypsin gene to the lung epithelium in vivo," *Science*, 252:431–434, 1991.

Rosenfeld et al., "In vivo transfer of the human cystic fibrosis transmembrane conductance regulator gene to the airway epithelium," *Cell*, 68:143–155, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Nat'l Acad. Sci. USA*, 86:9079–9083, 1989.

Samulski et al., *J. Virol.*, 61(10):3096–3101, 1987.

Sarver et al., "Ribozymes as potential anti-HIV-1 therapeutic agents," *Science*, 247:1222–1225, 1990.

Scanlon et al., "Ribozyme-mediated cleavages of c-fos MRNA reduce gene expression of DNA synthesis enzymes and metallothionein," *Proc. Natl. Acad Sci. USA*, 88:10591–10595, 1991.

Schall, "Chemotactic Cytokines: Targets for therapeutic development. international business communications," Southborough, Mass., pp 180–270, 1994.

Senkevich et al., "Genome sequence of a human tumorigenic poxvirus: Prediction of specific host response-evasion genes," *Science*, 273:813–816, 1996.

Smith et al., "Cutaneous findings in HIV-1-positive patients: a 42-month prospective study," *J. Am. Acad. Dermatol.*, 31:746–754, 1994.

Sozzani et al., "Receptor expression and responsiveness of human dendritic cells to a defined set of CC and CXC chemokines," *J. Immunol.*, 159:1993–2000, 1997.

Stewart and Young "Solid phase peptide synthesis," 2d. ed., Pierce Chemical Co., 1984.

Stratford-Perricaudet and Perricaudet, "Gene transfer into animals: the promise of adenovirus," p. 51–61, In: *Human Gene Transfer*, Cohen-Haguenauer and Boiron (Eds), Editions John Libbey Eurotext, France, 1991.

Stratford-Perricaudet et al., "Evaluation of the transfer and expression in mice of an enzyme-encoding gene using a human adenovirus vector," *Hum. Gene. Ther.*, 1:241–256, 1990.

Takematsu and Tagami, "Proinflammatory properties of molluscum bodies," *Arch. Dermatol. Res.*, 287:102–016, 1994.

Tam et al., *J. Am. Chem. Soc.*, 105:6442, 1983.

Temin, "Retrovirus vectors for gene transfer: Efficient integration into and expression of exogenous DNA in vertebrate cell genome," In: *Gene Transfer*, Kucherlapati (ed.), New York: Plenum Press, pp. 149–188, 1986.

Thompson et al., "Molecular epidemiology of Australian isolates of molluscum contagiosum," *J. Med. Virol.*, 32:1–9, 1990.

Thomson, "The Cytokine Handbook," 2d Ed. Academic Press, New York, 1994.

Top et al., "Immunization with live types 7 and 4 adenovirus vaccines. II. Antibody response and protective effect against acute respiratory disease due to adenovirus type 7," *J. Infect. Dis.*, 124:155–160, 1971.

Tur-Kaspa et al., "Use of electroporation to introduce biologically active foreign genes into primary rat hepatocytes," *Mol. Cell Biol.*, 6:716–718,1986.

Twyman and Jones, "The regulation of neuron-specific gene expression in the mammalian nervous system," *J. Neurogenectics*, 10:67–101, 1995.

U.S. Pat. No. 4,196,265
U.S. Pat. No. 5,354,855
Varmus et al., "Retroviruses as mutagens: Insertion and excision of a nontransforming provirus alter the expression of a resident transforming provirus," *Cell,* 25:23–36, 1981.
Viac and Chardonnet, "Immunocompetent cells and epithelial cell modifications in molluscum contagiosum," *J. Cutan. Pathol.,* 17:202–205, 1990.
Wagner et al., *Proc. Natl. Acad. Sci. USA,* 87(9):3410–3414, 1990.
Weiss et al., "An essential role for CD44 variant isoforms in epidermal Langerhans cell and blood dendritic cell function," *J. Cell. Biol.,* 137:1137–1147, 1997.
Wolpe et al., "Macrophages secrete a novel heparin-binding protein with inflammatory and neutrophil chemokinetic properties," *J. Exper. Med.,* 167:570–581, 1988.
Wong et al., "Appearance of β-lactamase activity in animal cells upon liposome mediated gene transfer," *Gene,* 10:87–94, 1980.
Wu and Wu, "Evidence for targeted gene delivery to HepG2 hepatoma cells in vitro," *Biochemistry,* 27:887–892, 1988.
Wu and Wu, "Receptor-mediated in vitro gene transfections by a soluble DNA carrier system," *J. Biol. Chem.,* 262:4429–4432, 1987.
Wu and Wu, Adv. *Drug Delivery Rev.,* 12:159–167, 1993.
Xiao et al., "Efficient long-term gene transfer into muscle tissue of immunocompetent mice by adeno-associated virus vector," *J. Virol.,* 70:8098–8108, 1996.
Yang et al., "In vivo and in vitro gene transfer to mammalian somatic cells by particle bombardment," *Proc. Natl. Acad. Sci USA,* 87:9568–9572, 1990.
Zelenin et al., "High-velocity mechanical DNA transfer of the chloramphenicol acetyltransferase gene into rodent liver, kidney and mammary gland cells in organ explants and in vivo," *FEBS Lett.,* 280:94–96, 1991.

What is claimed is:

1. An isolated and purified nucleic acid encoding a protein comprising an amino acid sequence as set forth in SEQ ID NO:2.

2. The nucleic acid of claim 1, wherein the nucleic acid sequence is as set forth in SEQ ID NO:1.

3. An expression construct comprising a vector comprising an isolated polynucleotide encoding a protein comprising an amino acid sequence as set forth in SEQ ID NO:2 or SEQ ID NO:4 and a promoter operably linked to said isolated polynucleotide.

4. The expression construct of claim 3, wherein said vector is a viral vector.

5. The expression construct of claim 4, wherein said viral vector is selected from the group consisting of a retroviral vector, an adenoviral vector, a herpesviral vector, adeno-associated viral vector and a cytomegaloviral vector.

6. The expression construct of claim 1, wherein the viral vector further comprises a polyadenylation signal.

7. The expression construct of claim 3, wherein said MCV viral protein has an amino acid sequence as set forth in SEQ ID NO:2.

8. The expression construct of claim 7, wherein said MCV protein is encoded by a nucleic acid sequence as set forth in SEQ ID NO:1.

9. The expression construct of claim 3, wherein said MCV protein has an amino acid sequence set forth in SEQ ID NO:2.

10. The expression construct of claim 9, wherein said MCV protein is encoded by a nucleic acid sequence as set forth in SEQ ID NO:3.

11. The expression construct of claim 3, wherein said MCV protein has an amino acid sequence set forth in SEQ ID NO:4.

12. A recombinant host cell comprising a cell with a vector comprising an expression region encoding a protein comprising an amino acid sequence as set forth in SEQ ID NO:2 or SEQ ID NO:4 operatively linked to a promoter.

13. The recombinant host cell of claim 12, wherein said MCV protein has an amino acid sequence as set forth in SEQ ID NO:2.

14. The recombinant host cell of claim 13, wherein said MCV protein is encoded by a nucleic acid sequence as set forth in SEQ ID NO:1.

15. The recombinant host cell of claim 12, wherein said MCV protein has an amino acid sequence as set forth in SEQ ID NO:4.

16. The recombinant host cell of claim 15, wherein said MCV protein is encoded by a nucleic acid sequence as set forth in SEQ ID NO:3.

17. A pharmaceutical composition comprising:
  (i) a vector construct comprising an expression region encoding a protein comprising an amino acid sequence as set forth in SEQ ID NO:2 or SEQ ID NO:4 under the control of a promoter active in eukaryotic cells; and
  (ii) a pharmaceutically acceptable carrier, excipient or diluent.

18. The pharmaceutical composition of claim 17, wherein said MCV protein has an amino acid sequence as set forth in SEQ ID NO:2.

19. The pharmaceutical composition of claim 18, wherein said MCV protein is encoded by a nucleic acid sequence as set forth in SEQ ID NO:1.

20. The pharmaceutical composition of claim 17, wherein said MCV protein has an amino acid sequence as set forth in SEQ ID NO:4.

21. The pharmaceutical composition of claim 20, wherein said MCV protein is encoded by a nucleic acid sequence as set forth in SEQ ID NO:3.

\* \* \* \* \*

UNITED STATES PATENT AND TRADEMARK OFFICE
CERTIFICATE OF CORRECTION

PATENT NO. : 6,281,200 B1
DATED : August 28, 2001
INVENTOR(S) : Kenneth H. Fife, Michell D. Krathwohl, Robert Hromas, Darron R. Brown and Hal E. Broxmeyer It is certified that error appears in the above-identified patent and that said Letters Patent is hereby corrected as shown below:

<u>Title page,</u>
Item [75], Inventors, please delete "Michell" and insert -- Mitchell -- therefor.
Item [60], Related US Application Data, please delete "15" and insert -- 13 -- therefor.

<u>Column 77,</u>
Line 66, please delete "1" and insert -- 3 -- therefor.

Signed and Sealed this

Fifth Day of November, 2002

Attest:

Attesting Officer

JAMES E. ROGAN
*Director of the United States Patent and Trademark Office*

SEQUENCE LISTING

<160> NUMBER OF SEQ ID NOS: 30

<210> SEQ ID NO 1
<211> LENGTH: 315
<212> TYPE: DNA
<213> ORGANISM: Molluscum contagiosum virus

<400> SEQUENCE: 1

```
atgagggcca gagccgtctt cgcgagcgtt gtcttgacgc tgttacttgc actaccgcga      60
ccgggagtgt cactctcgag acggaaatgt tgtttgaatc ctacaaatcg tccgataccg     120
aggcctttac tgcaagatct agacaaagtc gattatcagc cgatgggaca tgactgcgga     180
cgggaagctt tcagagtgac gctgcaagac ggaagacaag gctgtgttag cgttggtaac     240
cagagtttac tagactggct gaagggacac aaggatctct gcccgcggat gtggcccggg     300
tgcgagtctc tgtaa                                                      315
```

<210> SEQ ID NO 2
<211> LENGTH: 104
<212> TYPE: PRT
<213> ORGANISM: Molluscum contagiosum virus

<400> SEQUENCE: 2

```
Met Arg Ala Arg Ala Val Phe Ala Ser Val Val Leu Thr Leu Leu Leu
 1               5                  10                  15

Ala Leu Pro Arg Pro Gly Val Ser Leu Ser Arg Arg Lys Cys Cys Leu
            20                  25                  30

Asn Pro Thr Asn Arg Pro Ile Pro Arg Pro Leu Leu Gln Asp Leu Asp
        35                  40                  45

Lys Val Asp Tyr Gln Pro Met Gly His Asp Cys Gly Arg Glu Ala Phe
    50                  55                  60

Arg Val Thr Leu Gln Asp Gly Arg Gln Gly Cys Val Ser Val Gly Asn
65                  70                  75                  80

Gln Ser Leu Leu Asp Trp Leu Lys Gly His Lys Asp Leu Cys Pro Arg
                85                  90                  95

Met Trp Pro Gly Cys Glu Ser Leu
            100
```

<210> SEQ ID NO 3
<211> LENGTH: 315
<212> TYPE: DNA
<213> ORGANISM: Molluscum contagiosum virus

<400> SEQUENCE: 3

```
atgaggggcg agacgtcttc cgcgagcgtt gtcttgatgc tgttacttgc actaccgcga      60
ccgggagtgt cactcgcgag acggaaatgt tgtttgaatc ccacaaatcg tccgatcccg     120
aatcctttac tgcaagatct atcacgcgtc gactatcagg cgataggaca tgactgcgga     180
cgggaagctt tcagagtgac gctgcaagac ggaagacaag gctgcgttag cgttggtaac     240
aagagcttac tagactggct tcggggacac aaggatctct gccctcagat atggtccggg     300
tgcgagtctc tgtaa                                                      315
```

<210> SEQ ID NO 4
<211> LENGTH: 104
<212> TYPE: PRT
<213> ORGANISM: Molluscum contagiosum virus

<400> SEQUENCE: 4

```
Met Arg Gly Gly Asp Val Phe Ala Ser Val Val Leu Met Leu Leu Leu
  1               5                  10                  15

Ala Leu Pro Arg Pro Gly Val Ser Leu Ala Arg Arg Lys Cys Cys Leu
             20                  25                  30

Asn Pro Thr Asn Arg Pro Ile Pro Asn Pro Leu Leu Gln Asp Leu Ser
         35                  40                  45

Arg Val Asp Tyr Gln Ala Ile Gly His Asp Cys Gly Arg Glu Ala Phe
     50                  55                  60

Arg Val Thr Leu Gln Asp Gly Arg Gln Gly Cys Val Ser Val Gly Asn
 65                  70                  75                  80

Lys Ser Leu Leu Asp Trp Leu Arg Gly His Lys Asp Leu Cys Pro Gln
                 85                  90                  95

Ile Trp Ser Gly Cys Glu Ser Leu
            100
```

<210> SEQ ID NO 5
<211> LENGTH: 99
<212> TYPE: PRT
<213> ORGANISM: Homo sapiens

<400> SEQUENCE: 5

```
Met Lys Val Ser Ala Ala Leu Leu Cys Leu Leu Leu Thr Val Ala Ala
  1               5                  10                  15

Phe Ser Thr Glu Val Leu Ala Gln Pro Asp Ala Ile Asn Ser Gln Val
             20                  25                  30

Ala Cys Cys Tyr Thr Phe Asn Ser Lys Lys Ile Ser Met Gln Arg Leu
         35                  40                  45

Met Asn Tyr Arg Arg Val Thr Ser Ser Lys Cys Pro Lys Glu Ala Val
     50                  55                  60

Ile Phe Lys Thr Ile Leu Gly Lys Glu Leu Cys Ala Asp Pro Lys Gln
 65                  70                  75                  80

Lys Trp Val Gln Asp Ser Ile Asn Tyr Leu Asn Lys Asn Gln Thr
                 85                  90                  95

Pro Lys Pro
```

<210> SEQ ID NO 6

-continued

<211> LENGTH: 92
<212> TYPE: PRT
<213> ORGANISM: Homo sapiens

<400> SEQUENCE: 6

Met Lys Leu Cys Val Thr Val Leu Ser Leu Leu Met Leu Val Ala Ala
1 5 10 15

Phe Cys Ser Pro Ala Leu Ser Ala Pro Met Gly Ser Asp Pro Pro Thr
20 25 30

Ala Cys Cys Phe Ser Tyr Thr Ala Arg Lys Leu Pro Arg Asn Phe Val
35 40 45

Val Asp Tyr Tyr Glu Thr Ser Ser Leu Cys Ser Gln Pro Ala Val Val
50 55 60

Phe Gln Thr Lys Arg Ser Lys Gln Val Cys Ala Asp Pro Ser Glu Ser
65 70 75 80

Trp Val Gln Glu Tyr Val Tyr Asp Leu Glu Leu Asn
85 90

<210> SEQ ID NO 7
<211> LENGTH: 92
<212> TYPE: PRT
<213> ORGANISM: Homo sapiens

<400> SEQUENCE: 7

Met Gln Val Ser Thr Ala Ala Leu Ala Val Leu Leu Cys Thr Met Ala
1 5 10 15

Leu Cys Asn Gln Phe Ser Ala Ser Leu Ala Ala Asp Thr Pro Thr Ala
20 25 30

Cys Cys Phe Ser Tyr Thr Ser Arg Gln Ile Pro Gln Asn Phe Ile Ala
35 40 45

Asp Tyr Phe Glu Thr Ser Ser Gln Cys Ser Lys Pro Gly Val Ile Phe
50 55 60

Leu Thr Lys Arg Ser Arg Gln Val Cys Ala Asp Pro Ser Glu Glu Trp
65 70 75 80

Val Gln Lys Tyr Val Ser Asp Leu Glu Leu Ser Ala
85 90

<210> SEQ ID NO 8
<211> LENGTH: 17
<212> TYPE: DNA
<213> ORGANISM: Molluscum contagiosum virus

<400> SEQUENCE: 8
ccaagaggac gagctaa 17

<210> SEQ ID NO 9
<211> LENGTH: 20
<212> TYPE: DNA
<213> ORGANISM: Molluscum contagiosum virus

<400> SEQUENCE: 9
gttctcctgc tccatgacga 20

<210> SEQ ID NO 10
<211> LENGTH: 5
<212> TYPE: PRT
<213> ORGANISM: Homo sapiens

<400> SEQUENCE: 10

Gln Pro Asp Ala Ile

<210> SEQ ID NO 11
<211> LENGTH: 21
<212> TYPE: DNA
<213> ORGANISM: Molluscum contagiosum virus

<400> SEQUENCE: 11
ctcgcgagac ggaaatgttg t                                    21

<210> SEQ ID NO 12
<211> LENGTH: 7
<212> TYPE: PRT
<213> ORGANISM: Molluscum contagiosum virus

<400> SEQUENCE: 12

Leu Ala Arg Arg Lys Cys Cys
 1               5

<210> SEQ ID NO 13
<211> LENGTH: 24
<212> TYPE: DNA
<213> ORGANISM: Molluscum contagiosum virus

<400> SEQUENCE: 13
atcctcgcga gacggaaatg ttgt                                 24

<210> SEQ ID NO 14
<211> LENGTH: 8
<212> TYPE: PRT
<213> ORGANISM: Molluscum contagiosum virus

<400> SEQUENCE: 14

Ile Leu Ala Arg Arg Lys Cys Cys
 1               5

<210> SEQ ID NO 15
<211> LENGTH: 27
<212> TYPE: DNA
<213> ORGANISM: Molluscum contagiosum virus

<400> SEQUENCE: 15
gcgatcctcg cgagacggaa atgttgt                              27

<210> SEQ ID NO 16
<211> LENGTH: 9
<212> TYPE: PRT
<213> ORGANISM: Molluscum contagiosum virus

<400> SEQUENCE: 16

Ala Ile Leu Ala Arg Arg Lys Cys Cys
 1               5

<210> SEQ ID NO 17
<211> LENGTH: 30
<212> TYPE: DNA
<213> ORGANISM: Molluscum contagiosum virus

<400> SEQUENCE: 17
gacgcgatcc tcgcgagacg gaaatgttgt                           30

<210> SEQ ID NO 18
<211> LENGTH: 10
<212> TYPE: PRT

```
<213> ORGANISM: Molluscum contagiosum virus

<400> SEQUENCE: 18

Asp Ala Ile Leu Ala Arg Arg Lys Cys Cys
  1               5                  10

<210> SEQ ID NO 19
<211> LENGTH: 33
<212> TYPE: DNA
<213> ORGANISM: Molluscum contagiosum virus

<400> SEQUENCE: 19
cccgacgcga tcctcgcgag acggaaatgt tgt                                   33

<210> SEQ ID NO 20
<211> LENGTH: 11
<212> TYPE: PRT
<213> ORGANISM: Molluscum contagiosum virus

<400> SEQUENCE: 20

Pro Asp Ala Ile Leu Ala Arg Arg Lys Cys Cys
  1               5                  10

<210> SEQ ID NO 21
<211> LENGTH: 36
<212> TYPE: DNA
<213> ORGANISM: Molluscum contagiosum virus

<400> SEQUENCE: 21
caacccgacg cgatcctcgc gagacggaaa tgttgt                                36

<210> SEQ ID NO 22
<211> LENGTH: 12
<212> TYPE: PRT
<213> ORGANISM: Molluscum contagiosum virus

<400> SEQUENCE: 22

Gln Pro Asp Ala Ile Leu Ala Arg Arg Lys Cys Cys
  1               5                  10

<210> SEQ ID NO 23
<211> LENGTH: 4
<212> TYPE: PRT
<213> ORGANISM: Homo sapiens

<400> SEQUENCE: 23

Lys Arg Ser Arg
  1

<210> SEQ ID NO 24
<211> LENGTH: 4
<212> TYPE: PRT
<213> ORGANISM: Molluscum contagiosum virus

<400> SEQUENCE: 24

Gln Asp Gly Arg
  1

<210> SEQ ID NO 25
<211> LENGTH: 30
<212> TYPE: DNA
<213> ORGANISM: Molluscum contagiosum virus

<400> SEQUENCE: 25
```

-continued

```
gtgacgctgc aagacggaag acaaggctgc                                          30

<210> SEQ ID NO 26
<211> LENGTH: 10
<212> TYPE: PRT
<213> ORGANISM: Molluscum contagiosum virus

<400> SEQUENCE: 26

Val Thr Leu Gln Asp Gly Arg Gln Gly Cys
 1               5                  10

<210> SEQ ID NO 27
<211> LENGTH: 30
<212> TYPE: DNA
<213> ORGANISM: Molluscum contagiosum virus

<400> SEQUENCE: 27
gcagccttgt cttccgtctt gcagcgtcac                                          30

<210> SEQ ID NO 28
<211> LENGTH: 30
<212> TYPE: DNA
<213> ORGANISM: Molluscum contagiosum virus

<400> SEQUENCE: 28
gtgacgctga aaggtcaag acaaggctgc                                           30

<210> SEQ ID NO 29
<211> LENGTH: 10
<212> TYPE: PRT
<213> ORGANISM: Molluscum contagiosum virus

<400> SEQUENCE: 29

Val Thr Leu Lys Arg Ser Arg Gln Gly Cys
 1               5                  10

<210> SEQ ID NO 30
<211> LENGTH: 30
<212> TYPE: DNA
<213> ORGANISM: Molluscum contagiosum virus

<400> SEQUENCE: 30
gcagccttgt cttgaccttt tcagcgtcac                                          30
```